United States Patent
Berlin et al.

[11] Patent Number: 5,468,858
[45] Date of Patent: Nov. 21, 1995

[54] N-ALKYL AND N-ACYL DERIVATIVES OF 3,7-DIAZABICYCLO-[3.3.1]NONANES AND SELECTED SALTS THEREOF AS MULTI-CLASS ANTIARRHYTHMIC AGENTS

[75] Inventors: Kenneth D. Berlin, Stillwater, Okla.; Gregory L. Garrison, Chelmsford, Mass.; Subbiah Sangiah, Stillwater, Okla.; Cyril R. Clarke, Perkins, Okla.; Chun-Lin Chen, Stillwater, Okla.; Ralph Lazzara, Oklahoma City, Okla.; Benjamin J. Scherlag, Oklahoma City, Okla.; Eugene S. Patterson, Oklahoma City, Okla.; George E. Burrows, Stillwater, Okla.

[73] Assignee: The Board of Regents of Oklahoma State University Physical Sciences, Stillwater, Okla.

[21] Appl. No.: 144,639

[22] Filed: Oct. 28, 1993

[51] Int. Cl.⁶ .................. C07D 471/08; C07D 495/20; A61K 31/435
[52] U.S. Cl. .................. 546/18; 546/114; 546/122
[58] Field of Search .................. 546/18, 122; 514/278, 514/300

[56] References Cited

U.S. PATENT DOCUMENTS

| | | | |
|---|---|---|---|
| 4,581,361 | 4/1986 | Berlin et al. | 514/301 |
| 4,778,892 | 10/1988 | Berlin et al. | 546/122 |
| 4,910,311 | 3/1990 | Berlin et al. | 546/122 |
| 4,980,468 | 12/1990 | Berlin et al. | 544/95 |
| 5,043,445 | 8/1991 | Berlin et al. | 544/231 |
| 5,084,572 | 1/1992 | Berlin et al. | 546/18 |
| 5,110,933 | 5/1992 | Berlin et al. | 546/114 |

OTHER PUBLICATIONS

R. Jeyaraman and S. Avila pp. 149–174 (1981) Chemistry of 3–Azabicyclo[3.3.1]nonanes/Chemical Reviews, vol. 81, No. 2.

N. S. Zefirov and V. A. Palyulin pp. 171–230 (1991) Conformational Analysis of Bicyclo[3.3.1]nonanes and Their Hetero Analogs, Topics in Stereochemistry, vol. 20, edited by Ernest L. Eliel and Samuel H. Wilen, Interscience–Wiley, Publishers, New York.

*Primary Examiner*—Mukund J. Shah
*Assistant Examiner*—Philip I. Datlow
*Attorney, Agent, or Firm*—Head & Johnson

[57] ABSTRACT

3,7-Diazabicyclo[3.3.1]nonanes and selected derivatives thereof of the general formula:

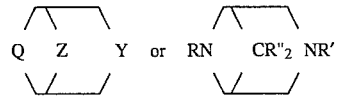

are disclosed as multiclass antiarrhythmic agents.

5 Claims, No Drawings

N-ALKYL AND N-ACYL DERIVATIVES OF 3,7-DIAZABICYCLO-[3.3.1]NONANES AND SELECTED SALTS THEREOF AS MULTI-CLASS ANTIARRHYTHMIC AGENTS

BACKGROUND OF THE INVENTION

1. Field of The Invention

This invention relates to antiarrhythmic compositions. Specifically, this invention relates to certain members of the family of 3,7-diazabicyclo[3.3.1]nonanes and highly selected derivatives thereof. 2. Description of the Prior Art 3-Azabicyclo[3.3.1]nonanes (3-ABN), 3,7-diazabicyclo[3.3.1]nonanes (3,7-DBCN), and certain derivatives thereof are known and have been documented in the literature in two reviews. These reviews are: (a) Chemical Reviews, Volume 81, No. 2, pages 149–174 (1981), entitled "Chemistry of 3-Azabicyclo[ 3.3.1]nonanes" by R. Jeyaraman and S. Avila and (b) Topics in Stereochemistry, Volume 20, E. L. Eliel and S. H. Wilen, Eds., Interscience-Wiley, Publishers, New York, Chapter entitled "Conformational Analysis of Bicyclo [3.3.1]nonanes and Their Hetero Analogs" by N. S. Zefirov and V. A. Palyulin, 1990. These reviews cover synthesis, reactions and certain aspects of the stereochemistry of such systems. These reviews also acknowledge that there is resemblance of the title compounds to aza- and diazaadamantanes in conformation and stereochemistry and that such systems have been obtained by Mannich reactions involving the condensations of certain ketones with a primary amine.

According to the chemical literature, some derivatives of 3-ABN and 3,7-DBCN have exhibited useful biological properties including analgesic, antiangina, antitussive, antipyretic, and antiarrhythmic agent (AAA) activity. In U.S. Pat. Nos. 4,581,361; 4,778,892; 4,910,311; 4,980,468; 5,043,445; 5,084,572; and 5, 110,933, for example, such materials are disclosed and claimed as antiarrhythmic agents.

The potential use of multi-class action antiarrhythmic agents [classification of action of antiarrhythmic agents has been made; see E. M. Vaughn Williams, "A Classification of Antiarrhythmic Drugs Reassessed After a Decade of New Drugs", Journal of Clinical Pharmacology, Volume 24, pages 129–147 (1984)] is now recognized. The few agents with some multi-class action have also been reviewed in "Cardiovascular Drugs", James A. Bristol, Ed., Wiley-Interscience Publishers, New York, 1986; chapter 2 entitled "Screening Methods and Test Models for Evaluation of Cardioactive Drugs", by Robert J. Lee, Richard J. Gorczynski, and Robert D. E. Reynolds. See also chapter 7 in this reference entitled "Antiarrhythmic Agents" which is authored by Johannes Hartenstein and Bernd Wagner.

Specifically, this invention is related to the above derivatives of 3,7-DBCN [1–46] and precursors [47– 100, 108–112] thereof for controlling life-threatening arrhythmias associated with the "sudden death syndrome" with individuals who experience heart attacks caused by coronary heart disease. The objective of the present invention is to provide useful compositions that display multi-class antiarrhythmic agent (AAA) activity. Fulfillment of this object and the presence and fulfillment of other objects will be apparent upon complete reading of the specifications and claims herein. The novelty of the invention lies in the the nonpredictable, multi-class AAA activity induced by very special substituents in the compositions.

SUMMARY OF INVENTION

The present invention involves novel derivatives (salts) of 3,7-diazabicyclo[3.3.1]nonanes having the basic formula:

Q—Z—Y    HX [or 2 HX]

X = ClO$_4$, Br, Cl, HSO$_4$
citrate, fumarate, maleate

| Q | Z | Y | NUMBER |
|---|---|---|---|
| (H$_3$C)$_2$CHN | CH$_2$ | 4-NC(O)C$_6$H$_4$NO$_2$ | 1 |
| (H$_3$C)$_2$CHN | CH$_2$ | 4-NC(O)C$_6$H$_4$NH$_2$ | 2 |
| (H$_3$C)$_2$CHN | CH$_2$ | 4-NC(O)C$_6$H$_4$NHSO$_2$CH$_3$ | 3 |
| (H$_3$C)$_2$CHN | CH$_2$ | 4-NC(O)C$_6$H$_4$—F | 4 |
| (H$_3$C)$_2$CHN | CH$_2$ | 4-NC(O)C$_6$H$_4$—N(pyrrole) | 5 |
| (H$_3$C)$_2$CHN | CH$_2$ | 4-NCH$_2$C(O)C$_6$H$_4$—F | 6 |
| (H$_3$C)$_2$CHN | CH$_2$ | 4-NCH$_2$C(O)C$_6$H$_4$—N(pyrrole) | 7 |
| (H$_3$C)$_2$CHN | CH$_2$ | 4-NCH$_2$CH(OH)C$_6$H$_4$—N(pyrrole) | 8 |

-continued

| Q | Z | Y | NUMBER |
|---|---|---|---|
| | 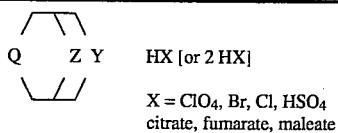 HX [or 2 HX]<br>X = ClO$_4$, Br, Cl, HSO$_4$<br>citrate, fumarate, maleate | | |
| (H$_3$C)$_2$CHN | CH | 4-NCH$_2$CH(OAc)C$_6$H$_4$—N⟨imidazole⟩ | 9 |
| (H$_3$C)$_2$CHN | CH$_2$ | NCH(CH$_3$)$_2$ | 10 |
| (H$_3$C)$_2$CHN | S–S (dithiolane) | NCH(CH$_3$)$_2$ | 11 |

SUMMARY OF INVENTION

| Q | Z | Y | NUMBER |
|---|---|---|---|
| ▷—CH$_2$N | CH$_2$ | NC(O)C$_6$H$_5$ | 12 |
| ▷—CH$_2$N | CH$_2$ | NCH$_2$C$_6$H$_5$ | 13 |
| ▷—CH$_2$N | CH$_2$ | 4-NC(O)C$_6$H$_4$—Cl | 14 |
| ▷—CH$_2$N | S–S (dithiolane) | NCH$_2$C$_6$H$_5$ | 15 |
| ▷—CH$_2$N | CH$_2$ | 4-NC(O)C$_6$H$_4$—F | 16 |
| ▷—CH$_2$N | CH$_2$ | 4-NC(O)C$_6$H$_4$—N⟨imidazole⟩ | 17 |
| ▷—CH$_2$N | CH$_2$ | 4-NCH$_2$C(O)C$_6$H$_4$—N⟨imidazole⟩ | 18 |
| ▷—CH$_2$N | CH$_2$ | 4-NCH$_2$CH(OH)C$_6$H$_4$—N⟨imidazole⟩ | 19 |
| ▷—CH$_2$N | CH$_2$ | 4-NC(O)C$_6$H$_4$—NO$_2$ | 20 |
| ▷—CH$_2$N | CH$_2$ | 4-NC(O)C$_6$H$_4$—NH$_2$ | 21 |
| ▷—CH$_2$N | CH$_2$ | 4-NC(O)C$_6$H$_4$—NHSO$_2$CH$_3$ | 22 |

Additional 3,7-DHBCNS-3

| Q | Z | Y | NUMBER |
|---|---|---|---|
| n-C$_3$H$_7$N | CH$_2$ | 4-NC(O)C$_6$H$_4$—F | 23 |
| n-C$_3$H$_7$N | CH$_2$ | 4-NC(O)C$_6$H$_4$—N⟨imidazole⟩ | 24 |

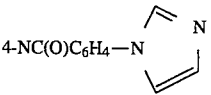

-continued

Q–Z–Y (cyclic) HX [or 2 HX]

X = ClO₄, Br, Cl, HSO₄, citrate, fumarate, maleate

| Q | Z | Y | NUMBER |
|---|---|---|---|
| n-C₃H₇N | CH₂ | 4-NCH(OH)C₆H₄—N(imidazole) | 25 |
| n-C₃H₇N | CH₂ | 4-NCH(OAc)C₆H₄—N(imidazole) | 26 |
| n-C₃H₇N | CH₂ | 4-NC(O)C₆H₄—NO₂ | 27 |
| n-C₃H₇N | CH₂ | 4-NC(O)C₆H₄—NH₂ | 28 |
| n-C₃H₇N | CH₂ | 4-NC(O)C₆H₄—NHSO₂CH₃ | 29 |
| n-C₃H₇N | CH₂ | 4-NCH₂C(O)C₆H₄—F | 30 |
| n-C₃H₇N | CH₂ | 4-NCH₂C(O)C₆H₄—N(imidazole) | 31 |
| n-C₃H₇N | CH₂ | 4-NCH₂C(O)C₆H₄—NO₂ | 32 |
| n-C₃H₇N | CH₂ | 4-NCH₂C(O)C₆H₄—NH₂ | 33 |
| n-C₃H₇N | CH₂ | 4-NCH₂C(O)C₆H₄—NHSO₂CH₃ | 34 |
| S | CH₂ | 4-NC(O)C₆H₄—F | 35 |
| S | CH₂ | 4-NC(O)C₆H₄—N(imidazole) | 36 |
| S | CH₂ | 4-NCH(OH)C₆H₄—N(imidazole) | 37 |
| S | CH₂ | 4-NCH(OAc)C₆H₄—N(imidazole) | 38 |
| S | CH₂ | 4-NC(O)C₆H₄—NO₂ | 39 |
| S | CH₂ | 4-NC(O)C₆H₄—NH₂ | 40 |
| S | CH₂ | 4-NC(O)C₆H₄—NHSO₂CH₃ | 41 |
| S | CH₂ | 4-NCH₂C(O)C₆H₄—F | 42 |
| S | CH₂ | 4-NCH₂C(O)C₆H₄—N(imidazole) | 43 |
| S | CH₂ | 4-NCH₂C(O)C₆H₄—NO₂ | 44 |
| S | CH₂ | 4-NCH₂C(O)C₆H₄—NH₂ | 45 |
| S | CH₂ | 4-NCH₂C(O)C₆H₄—NHSO₂CH₃ | 46 |

SUMMARY OF INVENTION

The present invention also provides for novel intermediates of the class of 3,7-diazabicyclo[3.3.1]-nonan-9-ones having the formula:

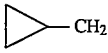

| R | Y | NUMBER |
|---|---|---|
| (H$_3$C)$_2$CHN | NCH(CH$_3$)$_2$ | 47 |
| 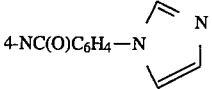—CH$_2$ | NCH$_2$C$_6$H$_5$ | 48 |

-continued

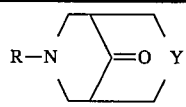

| R | Y | NUMBER |
|---|---|---|
| n-C$_3$H$_7$ | NCH$_2$C$_6$H$_5$ | 49 |

The invention further provides additional 3,7-diazabicyclo[3.3.1]nonanes of the formula:

| Q | Z | Y | NUMBER |
|---|---|---|---|
| (H$_3$C)$_2$CHN | CH$_2$ | 4-NC(O)C$_6$H$_4$NO$_2$ | 50 |
| (H$_3$C)$_2$CHN | CH$_2$ | 4-NC(O)C$_6$H$_4$NH$_2$ | 51 |
| (H$_3$C)$_2$CHN | CH$_2$ | 4-NC(O)C$_6$H$_4$NHSO$_2$CH$_3$ | 52 |
| (H$_3$C)$_2$CHN | CH$_2$ | 4-NC(O)C$_6$H$_4$—F | 53 |
| (H$_3$C)$_2$CHN | CH$_2$ | 4-NC(O)C$_6$H$_4$—N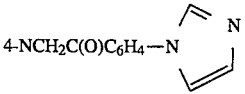 | 54 |
| (H$_3$C)$_2$CHN | CH$_2$ | 4-NCH$_2$C(O)C$_6$H$_4$—F | 55 |
| (H$_3$C)$_2$CHN | CH$_2$ | 4-NCH$_2$C(O)C$_6$H$_4$—N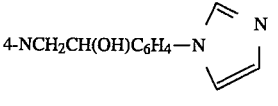 | 56 |
| (H$_3$C)$_2$CHN | CH$_2$ | 4-NCH$_2$CH(OH)C$_6$H$_4$—N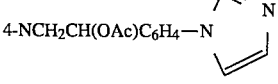 | 57 |
| (H$_3$C)$_2$CHN | CH$_2$ | 4-NCH$_2$CH(OAc)C$_6$H$_4$—N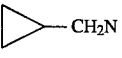 | 58 |
| (H$_3$C)$_2$CHN | CH$_2$ | NCH(CH$_3$)$_2$<br>Additional 3,7-DHBCNS-2 | 59 |
| 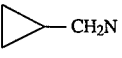—CH$_2$N | CH$_2$ | NC(O)C$_6$H$_5$ | 60 |
| 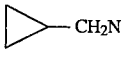—CH$_2$N | CH$_2$ | NCH$_2$C$_6$H$_5$ | 61 |
| 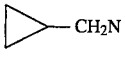—CH$_2$N | CH$_2$ | 4-NC(O)C$_6$H$_4$—Cl | 62 |
| 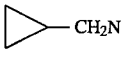—CH$_2$N | CH$_2$ | 4-NC(O)C$_6$H$_4$—F | 63 |
| 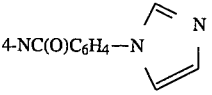—CH$_2$N | CH$_2$ | 4-NC(O)C$_6$H$_4$—N | 64 |

-continued

| Q | Z | Y | NUMBER |
|---|---|---|---|
| ▷—CH₂N | CH₂ | 4-NCH₂C(O)C₆H₄—N⟨imidazole⟩ | 65 |
| ▷—CH₂N | CH₂ | 4-NCH₂CH(OH)C₆H₄—N⟨imidazole⟩ | 66 |
| ▷—CH₂N | CH₂ | 4-NC(O)C₆H₄—NO₂ | 67 |
| ▷—CH₂N | CH₂ | 4-NC(O)C₆H₄—NH₂ | 68 |
| ▷—CH₂N | CH₂ | 4-NC(O)C₆H₄—NHSO₂CH₃ | 69 |

Additional 3,7-DHBCNS-3

| Q | Z | Y | NUMBER |
|---|---|---|---|
| n-C₃H₇N | CH₂ | 4-NC(O)C₆H₄—F | 70 |
| n-C₃H₇N | CH₂ | 4-NC(O)C₆H₄—N⟨imidazole⟩ | 71 |
| n-C₃H₇N | CH₂ | 4-NCH(OH)C₆H₄—N⟨imidazole⟩ | 72 |
| n-C₃H₇N | CH₂ | 4-NCH(OAc)C₆H₄—N⟨imidazole⟩ | 73 |
| n-C₃H₇N | CH₂ | 4-NC(O)C₆H₄—NO₂ | 74 |
| n-C₃H₇N | CH₂ | 4-NC(O)C₆H₄—NH₂ | 75 |
| n-C₃H₇N | CH₂ | 4-NC(O)C₆H₄—NHSO₂CH₃ | 76 |
| n-C₃H₇N | CH₂ | 4-NCH₂C(O)C₆H₄—F | 77 |
| n-C₃H₇N | CH₂ | 4-NCH₂C(O)C₆H₄—N⟨imidazole⟩ | 78 |
| n-C₃H₇N | CH₂ | 4-NCH₂C(O)C₆H₄—NO₂ | 79 |
| n-C₃H₇N | CH₂ | 4-NCH₂C(O)C₆H₄—NH₂ | 80 |
| n-C₃H₇N | CH₂ | 4-NCH₂C(O)C₆H₄—NHSO₂CH₃ | 81 |

Additional 3,7-DHBCNS-4

| Q | Z | Y | NUMBER |
|---|---|---|---|
| S | CH₂ | 4-NC(O)C₆H₄—F | 82 |
| S | CH₂ | 4-NC(O)C₆H₄—N⟨imidazole⟩ | 83 |
| S | CH₂ | 4-NCH(OH)C₆H₄—N⟨imidazole⟩ | 84 |
| S | CH₂ | 4-NCH(OAc)C₆H₄—N⟨imidazole⟩ | 85 |

-continued

|   | Q | Z | Y |   |
|---|---|---|---|---|
|   |   | \__/ |   |   |

| Q | Z | Y | NUMBER |
|---|---|---|---|
| S | CH$_2$ | 4-NC(O)C$_6$H$_4$—NO$_2$ | 86 |
| S | CH$_2$ | 4-NC(O)C$_6$H$_4$—NH$_2$ | 87 |
| S | CH$_2$ | 4-NC(O)C$_6$H$_4$—NHSO$_2$CH$_3$ | 88 |
| S | CH$_2$ | 4-NCH$_2$C(O)C$_6$H$_4$—F | 89 |
| S | CH$_2$ | 4-NCH$_2$C(O)C$_6$H$_4$—N(pyrrole) | 90 |
| S | CH$_2$ | 4-NCH$_2$C(O)C$_6$H$_4$—NO$_2$ | 91 |
| S | CH$_2$ | 4-NCH$_2$C(O)C$_6$H$_4$—NH$_2$ | 92 |
| S | CH$_2$ | 4-NCH$_2$C(O)C$_6$H$_4$—NHSO$_2$CH$_3$ | 93 |
|   |   | Additional 3,7-DHBCNS-5 |   |
| (H$_3$C)$_2$CHN | CH$_2$ | 4-NC(O)CH$_2$C$_6$H$_4$NO$_2$ | 94 |
| (H$_3$C)$_2$CHN | CH$_2$ | 4-NC(O)CH$_2$C$_6$H$_4$NO$_2$.HClO$_4$ | 95 |
| (H$_3$C)$_2$CHN | CH$_2$ | 4-NC(O)CH$_2$C$_6$H$_4$NH$_2$ | 96 |
| (H$_3$C)$_2$CHN | CH$_2$ | 4-NC(O)CH$_2$C$_6$H$_4$—NHSO$_2$CH$_3$ | 97 |
| (H$_3$C)$_2$CHN | CH$_2$ | 4-NC(O)CH$_2$C$_6$H$_4$—NHSO$_2$CH$_3$.HClO$_4$ | 98 |
| (H$_3$C)$_2$CHN | CH$_2$ | 4-NC(O)CH$_2$C$_6$H$_4$—NHAc | 99 |
| (H$_3$C)$_2$CHN | CH$_2$ | 4-NC(O)CH$_2$C$_6$H$_4$NHAc.HClO$_4$ | 100 |
| (H$_3$C)$_2$CHN | CH$_2$ | 4-NCH(O)C$_6$H$_4$—NHAc | 108 |
| (H$_3$C)$_2$CHN | CH$_2$ | 4-NCH(O)C$_6$H$_4$—NHAc.HClO$_4$ | 109 |
| (H$_3$C)$_2$CHN | CH$_2$ | 4-NCH$_2$CH(OH)C$_6$H$_4$—F | 110 |
| (H$_3$C)$_2$CHN | 1,3-dithiane | NCH(CH$_3$)$_2$ | 111 |
| cyclopropyl-CH$_2$N | 1,3-dithiane | NCH(CH$_3$)$_2$ | 112 |

DESCRIPTION OF THE PREFERRED EMBODIMENTS

The chemical compositions according to the preferred embodiments of this invention are heteronuclear ring organic compounds based on 3,7-diheterabicyclo[3.3.1] nonanes with the general structures as follows:

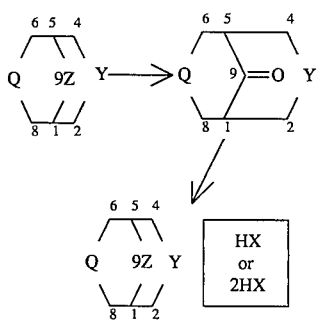

Most structures contain nitrogen at the 3,7-positions (1–34 and 47–81), but structures 35–46 and 82– 93 contain sulfur (S) at the 7-position. Substituents at the 3-position (Y) vary with N-acyl groups [1–5, 12, 14, 16, 17, 20–24, 27–29, 35, 36, 39–41, 50–54, 60, 62–64, 67–71, 74–76, 82, 83, 86– 88, 94–100,108,109] and N-alkyl groups [6–11, 13, 15, 18, 19, 25, 26, 30–34, 37, 38, 42–49, 55–59, 61, 65, 66, 72, 73, 77–81, 84, 85, 89–93, 110–112]. Substituents (Q) at the 7-position are either N-isopropyl, N-cyclopropylmethyl, N-benzyl or S. Salts [HX=hydroperchlorate, HCl, HBr, H$_2$SO$_4$, citrate, fumarate and maleate] are included. It is not intuitively obvious that the substituents described would elicit such remarkable multi-class AAA, and thus the agents described are novel. The bridging group (Z) is CH$_2$ group except for 11 and 15 in which a 9,9-(1,3-dithian-2-yl) group is present at the 9-position or in intermediates 47–49 where a carbonyl [C=O] group is present.

These compounds are the active ingredients for potential agents and/or intermediates for the active components of potential agents for the treatment of life-threatening rhythm disorders of the heart. They exhibit antiarrhythmic activity in animal models and are therefore viable candidates for the treatment of such disorders in humans who experience sudden heart attach or major infarctions of the heart.

In the Cardiac Arrhythmia Suppression Trial (CAST) ["The Cardiac Arrhythmia Suppression Trial Investigators, Preliminary Report: Effect of Encainide and Flecainide on Mortality in Randomized Trial of Arrhythmia Suppression After Myocardial Infarction" in the New England Journal Of Medicine, Volume 321, pages 406–412 (1989). See also "Mortality and Morbidity in Patients. Receiving Encainide, Flecainide, or Placebo-The Cardiac Arrhythmia Suppression Trials" in the New England Journal of Medicine, Volume 324, pages 781–788 (1991), by D. S. Echt, M D. Liebson, L. B. Mitchell, el. al. See also "CAST: Implications for Drug Development" in Clinical Pharmacology Therapy", Volume 47, pages 553–556 (1990) by R. L. Woosley], it was reported that the proarrhythmic effects of antiarrhythmie agents were responsible for inducing a statistically significant higher incidence of sudden cardiac death than the mortality rate of those patients taking a placebo agent [see also E. M. Vaughn-Williams "Significance of Classifying Antiarrhythmic Actions Since the Cardiac Arrhythmia Suppression Trial (CAST)" Journal of Clinical Pharmacology, Volume 31, pages 123–1356 (1991); P. J. Podrid and R.-I. Fogel, "Aggravation of Arrhythmia by Antiarrhythmic Drugs, and the Important Role Underlying Ischemia", American Journal of Cardiology, Volume 70, pages 100–102 (1992); H. L. Greene, D. M. Roden, R. J. Katz, R. L. Woosley, D. M. Salerno, R. W. Henthorn, and the CAST Investigators, "The Cardiac Arrhythmia Suppression Trial: First CAST . . . Then CAST-II" in the Journal of American College of Cardiology, Volume 19, pages 894–898 (1992)]. Members of the DBCN family members described herein this document do not commonly show significant proarrhythmic effects but do reduce rates of or abolish induced arrhythmias in animal models. Moreover, the commonly used agents in the CAST reagents as for the required key precursors of systems 47 and 48 have been expressed in U.S. Pat. No. 5,084,572. However, modifications have been necessary and these are delineated in this document. For example, and as outlined in Reaction Scheme A, the synthesis of the bicyclic ketones 47 and 48 originate from a Mannich or Mannich-type condensation starting from 1-isopropyl-4-piperidinone (101) or 1-benzyl-4-piperidinone (102). Ketones 101 and 102 reacted with isopropylamine or cyclopropylmethylamine and paraformaldehyde in the presence of acetic acid/hydrochloric acid/methanol to yield 47 and 48, respectively. The conditions are critical for good results. In addition, ketone 101 was allowed to react with benzylamine under similar conditions to give bicyclic system 103 {3-isopropyl- 7-benzyl-3,7-diazabicyclo[3.3.1]nonan- 9-one}. Reduction of bicyclic ketone 47 was effected with hydrazine in triethylene glycol/KOH media to generate 59 which was converted to its hydroperchlorate 10. In similar fashion, removal of the carbonyl oxygen atom in 103 was accomplished to give 104 { 3-isopropyl-7-benzyl-3,7-diazabicyclo-[ 3.3.1]nonane} as illustrated. Generation of an intermediate thioketal from 47 followed standard

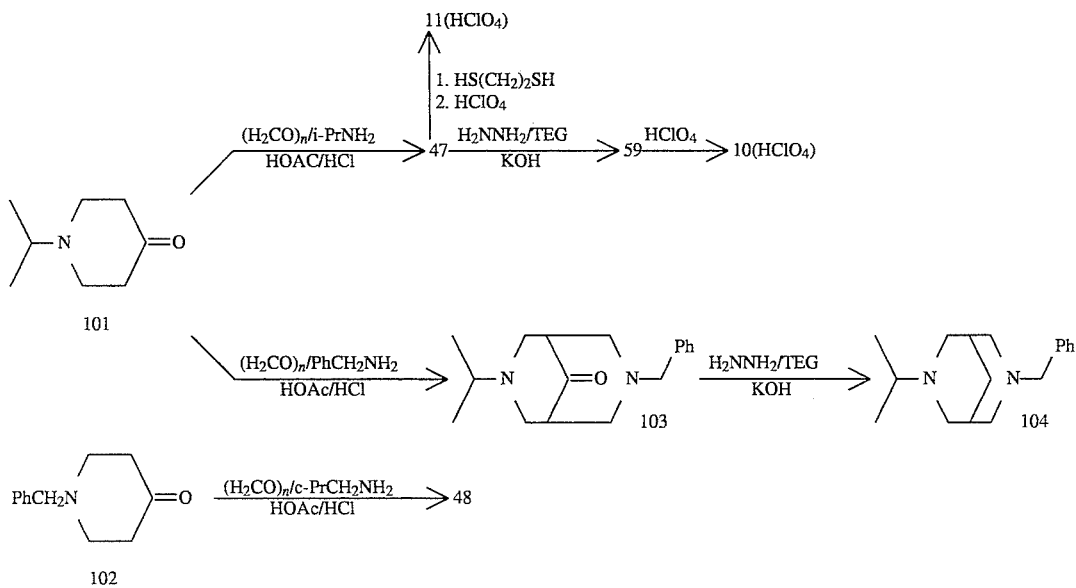

REACTION SCHEME A study depressed myocardial contractile function whereas the members of DBCN described in this document have been shown to increase mean blood pressure. Cardiac mechanical depression may excaberate the risk of sudden death, particularly in patients with preexisting coronary heart disease.

Representative reaction schemes are provided to illustrate the general methodology utilized in preparing the compounds to be claimed. Typical procedures using common procedures, but only salt 11 was isolated. The same procedure used to obtain 47, 48 and 103 can be used to obtain 49.

Diamine 104 is a key intermediate for the preparation of 1–9 and intermediates 50–58. Debenzylation of 104 is initiated as shown in Reaction Scheme B utilizing ammonium formate in the presence of palladium-on-carbon to yield 105. Aroylation of 105 with $4\text{-}O_2NC_6H_4C(O)Cl$ or $4\text{-}F\text{---}C_6H_4C(O)Cl$ as

REACTION SCHEME B

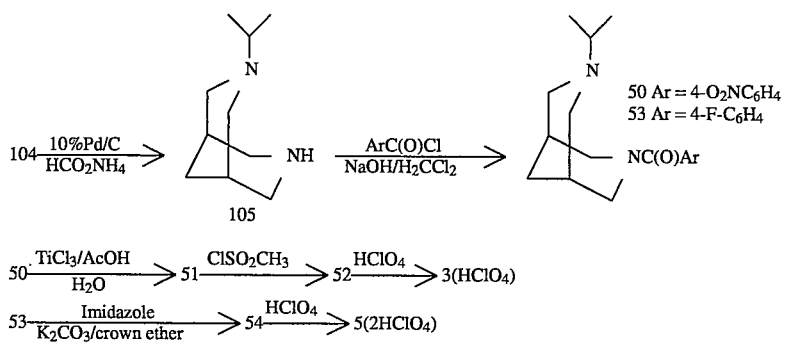

shown led to amides 50 and 53, respectively. Conversion of the nitro group in 50 to an amino group was done with $TiCl_3/AcOH$ to yield 51 which, in turn, was N-sulfonated with mesyl chloride to give 52. Addition of perchloric acid to this amide gave salt 3. Treatment of 53 with imidazole in the presence of $K_2CO_3$/18-crown-6 ether proceeded smoothly, and the intermediate 54 was converted directly to salt 5.

In Reaction Scheme C, bicyclic ketone 48 was reduced under the same conditions as described above to yield diamine 61. Formation of the salt 13 followed easily from 61. Conversion of ketone 48 to the intermediate thioketal was facile, and the latter was then converted to salt 15. Debenzylation of 61 was achieved as shown to yield key intermediate 106 which was used at once. Aroylation of 106 with benzoyl chloride or $4-ClC_6H_4C(O)Cl$ led to 60 and 62, respectively. Conversion of 60 and 62 to salts 12 and 14, respectively, followed in standard fashion.

usual manner or with imidazole/$K_2CO_3$ to 56 as shown in Reaction Scheme D. Treatment of 56 with $HClO_4$ led to salt 7. Reduction of 56 with sodium borohydride gave diamine 57 which was converted to salt 8.

REACTION SCHEME C

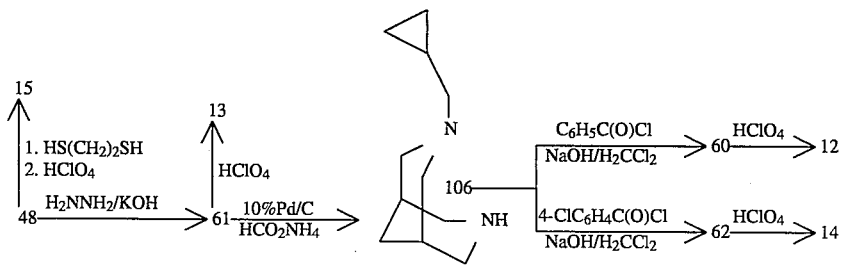

Alkylation of intermediate 105 with 4-fluorophenacyl chloride (107) gave 55 which was converted to salt 6 in the

REACTION SCHEME D

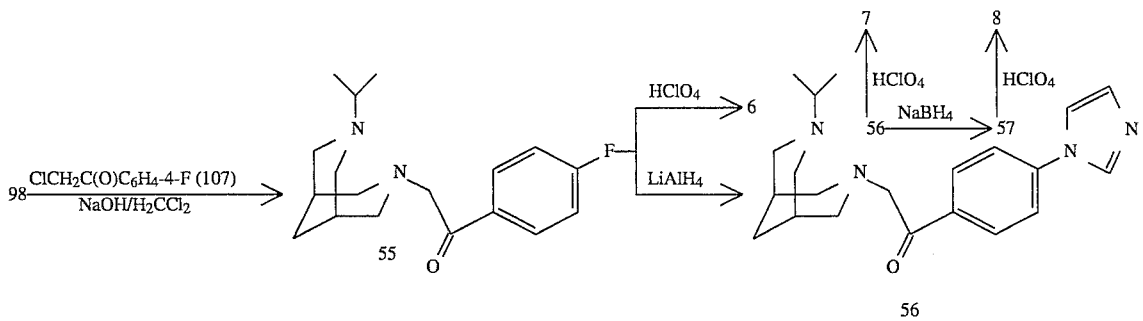

The following are representative examples of the compounds cited previously in this invention.

EXAMPLE I

3-Isopropyl-7-benzyl-3,7-diazabicyclo[3.3.1]nonan-9-one (103)

Ketone (103) was prepared by the method in U.S. Pat. No. 5,084,572

EXAMPLE II

3-Isopropyl-7-benzyl- 3,7-diazabicyclo[3.3.1]nonane (104)

Diamine (104) was prepared by the method in U.S. Pat. No. 5,084;572

EXAMPLE III

3-Isopropyl-3,7-diazabicyclo[3.3.1]nonane (105)

This diamine (105) was prepared by the method in U.S. Pat. No. 5,084,572

EXAMPLE IV 3-(4-Nitrobenzoyl)-7-isopropyl-3,7-diazabicyclo-[3.3.1]nonane Hydrochloride (1) and 3-(4-Nitrobenzoyl)-7-isopropyl-3,7-diazabicyclo-[3.3.1]nonane (50)

A flask was equipped with a magnetic stirrer, a condensor with $N_2$ inlet, an addition funnel and two glass stoppers. To a mixture of amine 105 (3.82 g, 22.70 mmol) in $H_2CCl_2$ (25 ml) and 10% NaOH (22.76 g, 56.80 mmol) was added dropwise a solution of 4-nitrobenzoyl chloride (4.63 g, 24.90 mmol) in $H_2CCl_2$ (15 ml) over a period of 15 min. Stirring of the mixture was continued for an additional 3 h under $N_2$. To the heterogenous mixture was added $H_2O$ (100 ml), and two layers were separated. Further extracts ($H_2CCl_2$, 3×50 ml) of the aqueous layer were combined, and the solution was dried ($Na_2SO_4$), filtered and concentrated to give a viscous yellow oil which solidified upon standing. This yellow solid was dissolved in ether, and the solution was filtered. The filtrate was concentrated and then dried by vacuum to give 6.79 g (94.3 %) of a light yellow solid 50; mp 119°–120° C. IR (KBr) 3090, 3005 (Ar-H), 2920, 2880, 2770 (C-H), 1635 (NC=O), 760 (C-H out of plane, para) cm$^{-1}$; $^1$H NMR (DCCl$_3$) δ0.56 (d, 3 H, CH$_3$ isopropyl), 0.69 (d, 3 H, CH$_3$ isopropyl), 1.34 [m, 2 H, H(9)$_{ax}$, H(5)], 1.61 lbs, 1 H, H(1)], 2.04–2.32 [m, 3 H, ring protons], 2.67 (dd, 2 H, ring protons), 2.94 (dd, 1 H, ring proton), 3.20 (d, 1 H, ring proton), 3.39 (d, 1 H, ring proton), 7.13 (d, 2 H, Ar-H), 7.85 (d, 2 H, Ar-H); $^{13}$C NMR (DCCl$_3$) ppm 15.89, 19.46 (CH$_3$ isopropyl), 28.81 29.57 C(1,5), 32.04 C(9), 46.55 (C-H isopropyl), 51.79, 52.31, 54.26, 54.85 C(2,4,6,8), 123.52, 127.60, 143.91, 147.62 (Ar-C), 167.58 (NC=O). Mass spectral (EI) data calcd for C$_{17}$H$_{23}$N$_3$O$_3$ m/e (M$^+$): 317.1739. Found: 317.1750. Anal. Calcd for C$_{17}$H$_{23}$N$_3$O$_3$: C, 64.33; H, 7.30; N, 13.24. Found: C, 64.06; H, 7.36; N, 12.97.

Gaseous HCl was generated in a flask containing solid NaCl which was treated with $H_2SO_4$ (15 ml) in a dropwise manner, and the gas generated was passed through a CaCl$_2$ drying tube. To a flask equipped with a magnetic stirrer and an ice bath was added HCl$_{(g)}$ to a chilled (5° C.) solution of amide 50 (2.5 g, 7.88 mmol) in ether (150 ml) over a 15 min period. The mixture was allowed to stir an additional 15 min at 0°–5° C. A white precipitate was filtered and washed with cold ether. The solid was recrystallized (methanol:ether, 1:1), and the white needles collected were washed (cold ether) and dried to give 2.09 g (74.9%) of salt 1; mp 258°–259° C. IR (KBr) 3410 (N-H), 3100, 3040 (Ar-H), 2950, 2860 (C-H), 1655 (NC=O) cm$^{-1}$; $^1$H NMR (D$_2$O) δ1.43 [d, 6 H, CH$_3$ isopropyl], 2.01 lbs, 2 H, H(9)], 2 H, H(1,5)], 3.39–3.67 [m, 9 H, H(2,4,6,8)] and C-H isopropyl], 7.71 [d, 2 H, Ar-H], 8.33 [d, 2 H, Ar-H], $^{13}$C NMR (D$_2$O) ppm 19.43 [CH$_3$ isopropyl], 29.56 [C(1,5,9)], 49.11, 53.32 [s, ring carbons],63.67 [C-H isopropyl], 126.89, 130.73, 143.84, 151.10 [Ar-C], 175.77 [NC=O]. Mass spectral (EI) data calcd for C$_{17}$H$_{24}$N$_3$O$_3$Cl m/z (M$^+$): 317.1739 (—HCl). Found: 317.1761. Anal. Calcd for C$_{17}$H$_{24}$N$_3$O$_3$Cl: C, 57.70; H, 6.84; N, 11.58. Found: C, 57.86; H, 6.72; N, 11.65.

EXAMPLE V 3-(4-Aminobenzoyl)-7-isopropyl-3,7-diazabicyclo-[3.3.1]nonane Hydrochloride (2) and 3-(4-Aminobenzoyl)-7-isopropyl-3,7-diazabicyclo-[3.3.1]nonane (51)

To a flask equipped with a magnetic stirrer was added amide 50 (9.17 g, 28.90 mmol) in AcOH:H$_2$O(1:1,100 ml). To this solution was added TiCl$_3$ (16%, 195.0 g, 202.3 mmol) in one portion, and the mixture was stirred at RT for 7 min. The deep purple solution was made basic (pH~12) with 20% NaOH until a blue color persisted. Extraction (H$_2$CCl$_2$, 4×90 ml) was followed by washing with H$_2$O (2× 100 ml) and brine (100 ml). After drying (Na$_2$SO$_4$), the solution was filtered and concentrated to give 7.34 g (86.2%)

of an off-white solid 51; mp 149°–150° C. IR (KBr) 3340, 3220 (N-H), 3060, 3020 (Ar-H), 2980, 2800 (C-H), 1640 (NC=O) cm$^{-1}$. $^1$H NMR (DCCl$_3$) δ0.98 (bs, 6 H, CH$_3$ isopropyl), 1.67 [m, 3 H, H(5), H(9)], 1.91 [s, 1 H, H(1)], 2.41 (bs, 2 H, ring proton), 2.72 (s, 1H, ring proton), 3.02 (bs, 2 H, ring protons), 3.31 (d, 1 H, ring proton), 3.83 (bs, 3 H, NH$_2$, ring proton), 4.70 (d, 1 H, ring proton), 6.62 (d, 2 H, Ar-H), 7.19 (d, 2 H, Ar-H); $^{13}$C NMR (DCCl$_3$) ppm 16.81, 18.79 (CH$_3$ isopropyl), 29.15, 29.79 C(1,5), 32.25 C(9), 46.61 (C-H isopropyl), 52.59, 54.22 C(2,4,6,8), 114.10 127.21, 128.68, 147.18 (Ar-C), 170.47 (NC=O). Anal. Calcd for C$_{17}$H$_{25}$N$_3$O: C, 71.05; H, 8.77; N, 14.62. Found: C, 70.67; H, 8.82; N, 14.28. The N-acetyl derivatve (108) was made from 51 and acetyl chloride in H$_2$CCl$_2$ in the standard fashion. This derivative (108) was converted to the hydroperchlorate (109) derivative (hygroscopic) in the usual manner. Anal. Calcd for C$_{19}$H$_{28}$ClN$_3$O$_6$·0.8: C, 51.036 H, 6.71. Found: 51.27; H, 6.63.

A flask was charged with amide 51 (2.0 g, 6.96 mmol) in ether and chilled to 5° C. HCl gas was added over a period of 10 minutes. The resulting white precipitate was filtered and washed with cold ether. Recrystallization (H$_3$COH:ether) of the solid followed by filtering and drying afforded (1.58 g, 70.2%) of salt 2; mp 209°–210° C. IR (KBr) 3400, 3160 (N-H), 3010, 2940, 2860 (C-H), 1630 (NC=O) cm$^{-1}$; $^1$H NMR (D$_2$O) δ1.45 [d, 6 H, CH$_3$ isopropyl], 2.03 lbs, 2 H, H(9)], 2.49 [bs, 2 H, H(1,5)]. 3.40–3.67 [m, 9 H, H(2,4,6,8) and C-H isopropyl], 4.63 [s, 2 H, N-H], 7.62 [m, 4 H, Ar-H]; $^{13}$C NMR (D$_2$O) ppm 18.83 [CH$_3$ isopropyl], 29.84, [C(1,5)], 30.14 [C(9)], 52.19, 55.26 [bs C(2,4,6,8)], 63.65 [C-H isopropyl], 124.20, 131.59, 135.29, 139.39 [Ar-C], 177.42 [NC=O]. Compound 2 was hygroscopic. Anal. Calcd for C$_{17}$H$_{26}$N$_3$OCl·0.9 H$_2$O: C, 54.23; H, 7.71;. Found: C, 54.56; H, 7.62.

EXAMPLE VI 3-(4-Methanesulfonamidebenzoyl)-7-isopropyl-3,7-diazabicyclo[3.3.1]nonane Hydroperchlorate (3) and 3-(4-Methanesulfonamidebenzoyl)-7-isopropyl-3,7-diazabicyclo[3.3.1]nonane (52)

A flask was equipped with an addition funnel, magnetic stirrer, condensor with N$_2$ inlet, and an ice bath. To a chilled (5° C.) solution of amide 51 (3.0 g, 10.44 mmol) and pyridine (0.87 g, 10.96 mmol) in H$_2$CCl$_2$ (20 ml) was added dropwise methanesulfonyl chloride (1.18 g, 10.34 mmol) in H$_2$CCl$_2$ (10 ml) over a 15 min period. After the addition was complete, the mixture was allowed to stir at RT overnight. Filtration of the solution removed traces of pyridine hydrochloride, and the filtrate was transferred to a separatory funnel. Extraction (1 N NaOH, 4×40 ml) was followed by neutralization (pH~7) of the aqueous phase, and the remaining organic layer was discarded. This neutral solution was extracted (H$_2$CCl$_2$, 4×40 ml), and the resulting solution was dried (Na$_2$SO$_4$) and filtered. After concentration, there was obtained 3.46 g (90.6%) of an off-white solid 52; mp 89°–91° C. IR (KBr) 3140 (N-H), 3040 (Ar-H), 2980, 2930, 2870, 2810 (C-H), 1610 (NC=O) cm$^{-1}$. $^1$H NMR (DCCl$_3$) δ0.97 (d, 3 H, CH$_3$ isopropyl), 1.08 (d, 3 H, CH$_3$ isopropyl), 1.69 lbs, 1 H, H(5)], 1.79 [bd, 2 H, H(9)], 1.98 [bs, 1 H, H(1)], 2.42 (d, 1 H, ring proton), 2.51 (d, 1 H, ring proton), 2.60 (m, 1 H, CH isopropyl), 2.74 (d, 1 H, ring proton), 3.03 (m, 5 H, ring protons, SO$_2$CH$_3$), 3.32 (d, 1 H, ring proton), 3.78 (d, 1 H, ring proton), 4.76 (d, 1 H, ring proton), 7.21–7.30 (q, 4 H, Ar-H); $^{13}$C NMR (DCCl$_3$) ppm 16.26, 19.16 (CH$_3$ isopropyl), 28.89, 29.55 [C(1,5)], 32.05 [C(9)], 39.18 [SO$_2$CH$_3$], 46.76 [C-H isopropyl], 52.11. 52.52, 54.19 [C(2,4,6,8)]. 119.80, 128.05, 128.16, 133.22, 138.21 [Ar-C], 169.63 [NC=O]. The compound 52 was used directly to make 3.

Solid 52 (3.1 g, 8.48 mmol) was dissolved in ethanol (95%, 50 ml), and the resulting solution was chilled (5° C.). With stirring, HClO$_4$ (60%, 1.77 g, 10.60 mmol) was added dropwise to the chilled solution over a period of 15 min. Stirring was continued an additional 10 min at this temperature. A white precipitate was filtered and recrystallized (H$_2$O) to give 1.97 g (49.9%) of white platelettes of 3; mp 267°– 268° C. IR (KBr) 3260, 3120 (N-H), 3010 (Ar-H), 2940, 2880 (C-H), 1630 (NC=O), 1100 (Cl-O) cm$^{-1}$. $^1$H NMR (DMSO-d$_6$) δ1.32 (dd, 2 H, CH$_3$ isopropyl), 1.69–1.87 [dd, 2 H, H(9)], 2.24 [m, 2 H, H(1,5)], 3.06 (s, 3 H, SO$_2$CH$_3$), 3.18–3.55 (m, 9 H, ring protons, C-H isopropyl), 7.24 (d, 2 H, Ar-H), 7.37 (d, 2 H, Ar-H), 7.93 (bs, 1 H, N-H), 10.05 (s, 1 H, CH$_3$SO$_2$N-H); $^{13}$C NMR (DMSO-d$_6$) ppm 26.48 (CH$_3$ isopropyl), 27.59 C(1,5,9), 39.52 (C-H isopropyl), 39.57 C(2,4,6,8), 59.53 (CH$_3$SO$_2$), 118.12, 128.81, 130.60, 139.53 (Ar-C), 172.62 (NC=O). Mass spectral (EI) data calcd for C$_{18}$H$_{28}$N$_3$SO$_7$Cl m/e (M$^+$): 365.1773 (—HClO$_4$). Found: 365.1775. Anal. Calcd for C$_{18}$H$_{28}$ClN$_3$SO$_7$; C, 46.40; H, 6.06; N, 9.02; S, 6.88. Found: C, 46.40; H, 6.01; N, 8.94; S, 7.07.

EXAMPLE VII 3-(4-Fluorobenzoyl)-7-isopropyl-3,7-diazabicyclo-[3.3.1]nonane Hydroperchlorate (4) and 3-(4-Fluorobenzoyl)-7-isopropyl-3,7-diazabicyclo-[3.3.1]nonane (53)

In flask equipped with a magnetic stirrer, an addition funnel, a condensor with N$_2$ inlet and a glass stopper were placed the amine 105 (2.53 g, 15.03 mmol) and NaOH (10%, 15.07 g, 37.58 mmol) in H$_2$CCl$_2$ (25 ml). A solution of 4-fluorobenzoyl chloride (2.62 g, 16.54 mmol) in H$_2$CCl$_2$ (15 ml) was added dropwise over a period of 0.5 h under N$_2$. The mixture was allowed to stir an additional 3 h. Addition of H$_2$O (50 ml) was followed by extraction with H$_2$CCl$_2$ (3×50 ml). Combined extracts were dried (Na$_2$SO$_4$), filtered, and concentrated to give a light yellow solid. Hash chromatography of the oil was performed on neutral alumina (50 g) with hexane:ethyl acetate (60:40) as the eluent. The filtrate was concentrated and placed under vacuum to give 3.88 g (89.0%) of amide 53 as a white solid; mp 87°–88° C. IR (KBr) 3090, 3005, 2975, 2930, 2860, 1630 (NC=O), 750 cm$^{-1}$. $^1$H NMR (DCCl$_3$) δ0.96 (d, 3 H, CH$_3$ isopropyl), 1.07 (d, 3 H, CH$_3$ isopropyl), 1.71 [m, 3 H, H(9), H(5)], 1.95 [s, 1 H, H(1)], 2.41– 2.72 (m, 3 H, ring protons), 3.03 (d, 2 H, ring protons), 3.31 (d, 1 H, ring proton), 3.72 (d, 1 H, ring proton), 4.74 (d, 1 H, ring proton), 7.08 (m, 2 H, Ar-H), 7.36 (m, 2 H, Ar-H); $^{13}$C NMR (DCCl$_3$) ppm 16.26, 19.18 (CH$_3$ isopropyl), 28.97, 29.69 C(1,5), 32.16 C(9), 46.59 (C-H isopropyl), 52.12, 52.49, 54.65 C(2,4,6,8), 114.96, 115.25, 128.77, 128.88, 133.60, 133.64 (Ar-C), 161.04, 164.33 (J=248.2 Hz, ArC-F), 169.07 (NC=O). Mass spectral (EI) data calcd for C$_{17}$H$_{23}$N$_2$OF m/z (M$^+$): 290.1794. Found: 290.1790. Anal. Calcd for C$_{17}$H$_{23}$N$_2$OF: C, 70.32; H, 7.98; N, 9.65. Found: C, 70.39; H, 8.03; N, 9.71.

To a chilled (5° C.) solution of amide 53 (1.0 g, 3.44 mmol) in ether contained in a flask was added dropwise HClO$_4$ (60%, 0.72 g, 4.30 mmol) over a period of 5 minutes. This precipitate was filtered and washed with cold ether. Recrystallization (methanol) of the precipitate was followed by filtration and drying to give g(1.03 g, 76.3%) of salt 4 as white platelettes; mp 246°–247° C. IR (KBr) 3120 (N-H), 3010 (Ar-H), 2940, 2880 (C-H), 1625 (NC=O) cm$^{-1}$; $^1$H NMR (D$_3$C-C≡N) δ1.38 (d, 6 H, CH$_3$ isopropyl), 1.81 [d, 1 H, H(5)], 2.29 [d, 3 H, H(5,9)], 3.34 [m, 5 H, ring protons, C-H isopropyl], 3.52 [bd, 4 H, ring protons], 7.17 [t, 2 H, Ar-H], 7.38 [m, 2 H, Ar-H]; $^{13}$C NMR (D$_3$CC≡N) ppm 16.72 [CH$_3$ isopropyl], 27.89 [C(1,5)], 28.99 [ C(9)], 50.34, 53.52 lbs, C(2,4,6,8)], 60.96 [C-H isopropyl], 116.29, 116.59, 118.01, 118.36, 130.65, 130.77, 132.78, 132.82 [Ar-C], 162.59, 165.88 [J=247.6 Hz, ArC-F], 174.13 [NC=O]. Mass specttral (El) data calcd for C$_{17}$H$_{24}$ClN$_2$O$_5$F m/z (M$^+$): 290.1855 (—HClO$_4$). Found: 290.1853. Anal. Calcd for C$_{17}$H$_{24}$ClN$_2$O$_5$F: C, 52.24; H, 6.19. Found: C, 52.46; H, 6.24.

EXAMPLE VIII

3-{4-(1H-Imidazol-1-yl)benzoyl]-7-isopropyl-3,7-diazabicyclo[3.3.1] nonane Dihydroperchlorate (5) and 3-[4-( 1H-Imidazol-1-yl)benzoyl]-7-isopropyl-3,7-diazabicyclo[3.3.1]-nonane (54)

A jacketed flask was equipped in the standard manner. To a solution of amide 53 (3.35 g, 11.54 mmol) in DMSO (50 ml) was added imidazole (1.18 g, 17.30 mmol), potassium carbonate (anhydrous, 1.67 g, 12.12 mmol), and 18-crown-6 (500 mg). The stirred mixture was heated at 110° C. for 40 h under N$_2$ with the use of boiling toluene in the jacket. Cooling the solution to RT was followed by addition of chilled H$_2$O (75 ml). Combined extracts (H$_2$CCl$_2$, 4×40 ml) of the suspension were washed with H$_2$O (80 ml) and saturated NaCl (80 ml); the solution was then dried (Na$_2$SO$_4$). Filtration and concentration gave a light yellow solid 54 which was dried on a vacuum pump overnight. Flash chromatography (neutral alumina) of the crude solid in solution using ethyl acetate:hexane (2:3) caused the starting material to be eluted first. With a more polar solvent system [ethyl acetate:methanol (30:1)] product 54 could be isolated (1.35 g, 35.1%) as an off white, gummy solid for which a melting point could not be determined since the material appeared to be hygroscopic. IR (KBr) 3400 (N-H), 3110 (Ar-H), 2975, 2910, 2800 (C-H), 1620 (NC=O), 735 (para) cm$^{-1}$. $^1$H NMR (DCCl$_3$) δ0.96–1.14 [ dd, 6 H, CH$_3$ isopropyl], 1.68 [dd, 1 H, H(9)], 1.81 [bs, 2 H, H(1,5)]. 2.02 [bs, 1 H, H(9)], 2.45 [d, 1 H, ring proton], 2.57 [d, 1 H, ring proton], 2.63 [m, 1 H, C-H isopropyl], 2.77 [d, 1 H, ring proton], 3.09 [d, 2 H, ring protons], 3.38 [d, 1 H, ring proton], 3.76 [d, 1 H, ring proton], 4.79 [d, 1 H, ring proton], 7.22[s, 1 H, C-H imidazole], 7.41–7.54 [dd, 4 H, Ar-H], 7.89 [s, 1 H, imidazole]; $^{13}$C NMR (CDCl$_3$) ppm 16.33,19.41 [CH$_3$ isopropyl], 29.03,29.78 [ C(1,5)], 32.26[C(9)], 46.72 [C-H isopropyl], 52.15, 52.61, 54.38, 54.82 [C(2,4,6,8)], 118.07 [C-H imidazole], 121.15, 128.54 [Ar-C], 130.60, 135.44 [C-H imidazole]. 136.91,137.43 [Ar-C], 168.80 [NC=O]. This material was convened directly to a salt.

Treatment of 54 (1.44 g, 4.25 mmol) with HClO$_4$ (60%, 1.6 mmol) at 5° C. (ice bath) produced a white precipitate. Filtration, followed by recrystallization (methanol) of the solid, gave white needles (1.14 g, 60.9%) of 5; mp 262°–263° C. IR (KBr) 3200 (N-H), 3005 (Ar-C), 2940, 2880 (C-H), 1645 (NC=O), 1100 (Cl-O) (cm$^{-1}$). $^1$H NMR (DMSO-d$_6$) δ1.33 [bs, 6 H, (H$_3$C)$_2$C], 2.34, 2.41 [d, 2 H, H(9)], 2.79 (bs, 1 H, NH), 3.03 [s, 2 H, H(1,5)], 3.23, 3.97 [bs, 9 H, H(2, 4, 6, 8), C-H isopropyl], 7.66 (d, 2 H, ArH), 7.94 (s, 1 H, C-H imidazole), 7.96 (d, 2 H, ArH), 8.32 (s, 1 H, C-H imidazole), 9.20 (s, 1 H, C-H imidazole); $^{13}$C NMR (DMSO-d$_6$) ppm 26.42, 27.36, 59.64 (ring carbons), 120.63, 121.35. 122.01, 128.74, 135.27, 137.49(Ar-C), 171.49 (NC=O); Mass spectral (El) data calcd for C$_{20}$H$_{28}$Cl$_2$N$_4$O$_9$ m/z (M$^+$): 338.2106 (–2 HClO$_4$). Found: 338.2099. Anal. Calcd for C$_{20}$H$_{28}$Cl$_2$N$_4$O$_9$; C, 44.54; H, 5.23; N, 10.38. Found: C, 44.75; H, 5.20; N, 10.20.

EXAMPLE IX

7-Isopropyl-3-(4-fluorophenacyl)-3,7-diazabicyclo-[3.3.1]nonane (55)

To a standard setup was added 2-chloro-4'-fluoroacetophenone (7.55 g, 43.8 mmol) and NaI (9.85 g, 65.7 mmol) in H$_3$CCN (30 ml) which was then heated for 30 minutes with stirrring. The solution was allowed to cool to room temperature (30 min) which was followed by dropwise addition of amine 105 (6.7 g, 39.8 mmol) to give a light yellow mixture which was stirred overnight. Filtration (suction) removed excess NaI and the filtrate was diluted with H$_2$O and transferred to a separatory funnel. The resulting homogenous solution (pH~5) was extracted (ether, 3×75 ml) with the latter being discarded, and the pH of the aqueous layer was adjusted to 12 using 10% NaOH. Extraction (ether, 3× 75 ml) of the aqueous layer was followed by another extraction (H$_2$CCl$_2$, 3×75 ml) and the ether extracts were discarded. The organic layer (H$_2$CCl$_2$) was dried (Na$_2$SO$_4$, 2 h), filtered, and concentrated (rotary evaporator) to give 2.9 g (86.1%) of amine 55 as a light yellow solid; mp 193°–194° C. IR (KBr) 3060, 3040 (Ar-H), 2940, 2805 (C-H), 1700 (C=O) cm$^{-1}$; $^1$H NMR (DCCl$_3$) d 1.45 (d, 6 H, CH$_3$ isopropyl), 1.81 [d, 1 H, H(9)$_{ax}$], 2.11 [d, 1 H, H(9)$_{eq}$], 2.32 lbs, 2 H, H(1,5)], 2.85 (d, 2 H, ring protons), 3.37 (d, 2 H, ring protons), 3.49 (d, 2 H, ring protons), 3.86 (m, 3 H, ring protons, C-H isopropyl), 4.18 (s, 2 H, ArC(O)CH$_2$), 7.15 (t, 2 H, Ar-H), 8.02 (m, 2 H, Ar-H); $^{13}$C NMR (DCCl$_3$) ppm 17.01 (CH$_3$ isopropyl), 28.04 [C(1,5)], 30.05 [C(9)], 53.74, 57.2257.34 (ring carbons, C-H isopropyl), 62.22 [ArC(O)CH$_2$], 115.58, 115.88, 130.57, 130.70, 131.22, 131.26 (Ar-C), 164.10, 167.49 (J= 265.8 Hz, ArC-F), 194.99 (C=O). Ketone 55 was slightly unstable, and thus was reduced to the corresponding alcohol 110.

EXAMPLE X

(±)-3-[(4'-Fluoro)-1-hydroxy-1-phenylethyl]-7-isopropyl-3,7-diazabicyclo[ 3.3.1]nonane (110)

To a standard setup was added solid LiAlH$_4$ (95%, 0,787 g, 19.7 mmol) in one portion. After purging the flask with N$_2$ for 10 min, tetrahydrofuran (10 ml) was poured slowly over the LiAlH$_4$ which resulted in a gray slurry. Ketone 55 (2.0 g, 6.57 mmol) was added portionwise over a period of 15 min, followed by heating the reaction mixture (40° C., 3 h) and then stirring at room temperature overnight. Excess LiAlH$_4$ was destroyed using EtOAc (10 ml) added dropwise to the chilled (5° C.) reaction mixture. Addition of 5% HCl (~15 ml) adjusted the aqueous solution to pH~2 which was then extracted (ether, 2× 30 ml) to remove small impurities and these ether extracts were discarded. After making the aqueous phase slightly basic (pH~8) using 10% NaOH (~10 ml), extraction (H$_2$CCl$_2$, 3×50 ml) was followed by washing the organic layer with H$_2$O (75 ml), said NaCl (75 ml), and dried (Na$_2$SO$_4$, 2 h). Filtration and concentration (rotary evaporator) resulted in 1.33 g (66.2%) of racemic alcohol 110 as a white solid; mp 53°–54° C. IR (film) 3225 (OH), 2930, 2800 (C-H), 1600 (C=C) cm$^{-1}$; $^1$H NMR (DCCl$_3$)

δ1.08 (d, 6 H, $CH_3$ isopropyl), 1.57 lbs, 2 H, H(9)], 1.87 lbs, 2 H, H(9)], 2.26 (m, 2 H, ring protons), 2.45 (d, 2 H, ring protons), 2.55 [dd,J= 4.09 Hz, 2 H, $ArCH(OH)CH_2$], 2.83 (bs, 2 H, ring protons), 3.07 (m, 3 H, ring protons, C-H isopropyl), 4.67 [dd, J= 4.09 Hz, 1 H, ArCH(OH)], 6.23 (bs, 1 H, O-H), 7.01 (t, 2 H, Ar-H), 7.35 (m, 2 H, Ar-H); $^{13}C$ NMR ($DCCl_3$) ppm 18.39, 18.69 ($CH_3$ isopropyl), 30.17, 30.90 [C(1,5)], 32.54 [C(9)], 54.07, 54.38, 54.61, 55.24 [C(2,4,6,8)1, 59.55 (C-H isopropyl), 64.47 [ArCH(OH)$CH_2$], 68.54 [ArC-H(OH)], 114.71, 114.99, 127.39, 127.49, 138.97, 139.00 (Ar-C), 160.28, 163.51 (J=243.9 Hz, ArC-F); Anal. Calcd for $C_{18}H_{27}FN_2O$: C, 70.56; H, 8.88. Found: C, 70.28; H, 9.00.

EXAMPLE XI 3,7-Diisopropyl-3,7-diazabicyclo[3.3.1]nonane Hydroperchlorate (10)

3,7-Diisopropyl-3,7-diazabicyclo[3.3.1]nonane (59)

A jacketed flask was equipped with a magnetic stirrer, a heating mantle, a condensor, a lower takeoff condensor with $N_2$ inlet and two glass stoppers. To a solution of ketone 47 (5.9 g, 20.3 mmol) in triethylene glycol (50 ml) was added KOH pellets (85%, 13.89 g, 210.9 mmol) and hydrazine (95%, 3.55 g, 105.19 mmol). The stirred mixture was heated at 200°–210° C. for 4 h under $N_2$ with the use of boiling tetralin in the jacket. Cooling the solution to RT was followed by addition of chilled $H_2O$. Combined extracts (ether, 4×80 ml) of the suspension were washed with 10% NaOH and saturated NaCl, was then dried ($Na_2SO_4$). Filtration and concentration gave an oil which was placed under vacuum. A new yellow oil 59 resulted (4.48 g, 81.1%). IR (KBr) 2975, 2900, 2820 (C-H), $cm^{-1}$. IR analysis of compound showed no carbonyl stretch spectrum, and thus 59 was used directly to prepare salt 10.

A flask was equipped with a magnetic stirrer and an ice bath. To a chilled (5° C.) solution of amine 59 (3.4 g, 16.16 mmol) in dry ether (150 ml) was added $HClO_4$ (60%, 3.4 g, 20.2 mmol) dropwise over a period of 15 min. The mixture was allowed to stir an additional 15 min at 0°–5° C. A white precipitate formed and was filtered and washed (cold ether, 30 ml). The solid was recrystallized (methanol), and white needles were collected and washed (cold methanol) and dried to give 3.63 g (72.3%) of salt 10 (hygroscopic); mp 211°–212° C. IR (KBr) 2985, 2940, 2850, 1090 (Cl-O) $cm^{-1}$; $^1H$ NMR ($D_3C-C≡N$) δ 1.14 [, d, 12 H, $CH_3$ isopropyl], 1.80 [bs, 2 H, H(1,5)], 2.21 [bs, 2 H, H(9)], 2.97 [d, 4 H, ring protons], 3.19 [m, 2 H, C-H isopropyl], 3.28 [d, 4 H, ring protons]; $^{13}C$ NMR ($D_3C-C≡N$) ppm 17.11 [$CH_3$ isopropyl], 28.56 [C(1,5)], 31.41 [C(9)], 54.26 [C(2,4,6,8)], 56.13 [C-H isopropyl]. Mass spectral (EI) data calcd for $C_{13}H_{27}N_2O_4Cl$ m/z ($M^+$): 210.2096. Found: 210.2096. Anal. Calcd for $C_{13}H_{27}N_2O_4Cl·0.2 H_2O$ C, 49.66; H, 8.78; N, 8.91. Found: C, 49.33; H, 8.52; N, 9.31.

EXAMPLE XII 3,7-Diisopropyl-9,9-(1,3-dithiolan-2-yl)-3,7-diazabicyclo[3.3.1]nonane Hydroperchlorate (11) and
3,7-Diisopropyl-9,9-(1,3-dithiolan-2-yl)-3,7-diazabicyclo[3.3.1]nonane (111)

A flask was equipped with a magnetic stirrer, condensor with a $N_2$ inlet, a Dean-Stark trap, and a heating mantle. After addition of the ketone 47 (8.0 g, 35.66 mmol), 1,2-ethanedithiol (33.59 g, 356.6 mmol), p-toluenesulfonic acid (16.28 g, 85.58 mmol) and benzene (200 ml) were added, and the resulting mixture was heated at reflux for 40 h. The solvent was then removed through a Dean-Stark trap, and the resulting oil was dissolved in $H_2O$. The aqueous layer was extracted (ether, 2×100 ml), the extracts being discarded. Basification (pH~12) of the aqueous solution was achieved using 10% NaOH, followed by extraction (ether, 4×75 ml). The organic layer was washed with NaOH (1 N) and then brine. After drying ($Na_2SO_4$) the solution, evaporation afforded 8.06 g (75.2%) of a light yellow oil which was 3,7-diisopropyl- 9,9-(1,3-dithiolan-2-yl)-3,7-diazabicyclo[3.3.1] nonane (111). IR (film) 2905, 2800 (C-H)$cm^{-1}$ 2905, 2800 (C-H). Since IR analysis showed no carbonyl band, the oil 111 was used directly to prepare 11 without further purification. $^1H$ NMR of this oil showed: ($DCCl_3$) δ1.03 [d, 12 H, $CH_3$ isopropyl], 2.26 [d, 4 H, ring protons], 2.77 [m, 2 H, C-H isopropyl], 2.89 [dd, 4 H, ring protons], 3.08 [s, 4 H, S-$CH_2$]; $^{13}C$ NMR ($DCCl_3$) ppm 17.97 [$CH_3$ isopropyl], 37.39 [C(1,5)], 43.11 [S-$CH_2$], 51.20 [C(2,4,6,8)], 53.21 [C-H isopropyl], 70.89 [C(9)].

Into a flask equipped with a magnetic stirrer and an ice bath was placed thioketal 111 (8.06 g, 26.82 mmol) in dry ether (100 ml), and the solution was cooled to 0°–5° C. To the stirred mixture was added dropwise $HClO_4$ (60%, 5.61 g, 33.52 mmol) over a period of 15 min. After stirring an additional 15 min at 5° C., a white precipitate was filtered and washed (cold ether). Recrystallization (methanol) afforded, after drying, hydroperchlorate 11 as white needles (6.72 g, 62.5%); mp 222.0°–223.0° C. IR (KBr) 2990, 2940, 2860, 1080 (Cl-O) $cm^{-1}$. $^1H$ NMR ($DCCl_3$) δ1.18 (d, 12 H, $CH_3$ isopropyl), 2.31 [bs, 2 H, H(1,5)], 3.32–3.57 [m, 15 H, N-H, $H(2,4,6,8)_{ax-eq}$, C-H isopropyl, S-$CH_2$]; $^{13}C$ NMR ($DCCl_3$) ppm 16.78 ($CH_3$ isopropyl), 39.29 C(1,5), 41.23 (S-$CH_2$), 52.29 C(2,4,6,8), 54.64 (C-H isopropyl), 70.22 C(9). Mass spectral (EI) data calcd for $C_{15}H_{29}N_2S_2O_4Cl$ m/e ($M^+$): 300.1694 (—$HClO_4$). Found: 300.1695. Anal. Calcd for $C_{15}H_{29}ClN_2S_2O_4$: C, 44.93; H, 7.29; N, 6.99; S, 15.99 Found: C, 45.10; H, 7.33; N, 6.91; S, 15.80.

EXAMPLE XIII

3-Benzoyl-7-cyclopropylmethyl-3,7-diazabicyclo[3.3.1]nonane Hydroperchlorate (12) and
3-Benzoyl-7-cyclopropylmethyl-3,7-diazabicyclo[3.3.1]nonane (60)

Into a flask equipped with a magnetic stirrer, an addition funnel, a condensor with $N_2$ inlet, and a glass stopper were placed the amine 106 (5.50 g, 30.51 mmol) and NaOH (10%, 30.60 g, 76.28 mmol) in $H_2CCl_2$ (25 ml). A solution of benzoyl chloride (4.72 g, 33.56 mmol) in $H_2CCl_2$ (15 ml) was added dropwise over a period of 0.5 h under $N_2$. The mixture was allowed to stir an additional 3 h. Addition of $H_2O$ (50 ml) was followed by extraction with $H_2CCl_2$ (3×50 ml). Combined extracts were dried ($Na_2SO_4$), filtered, and concentrated to give a yellow oil. Flash chromatography of the oil was performed on neutral alumina (50 g, 60-ml fritted funnel, suction) with ethyl acetate as the eluent. The filtrate was concentrated and placed under vacuum to give 7.15 g (82.4%) of amide 60 as an oil which was used directly to prepare 12. IR (film) 3090, 3005 (Ar-H), 2920, 2860, 2775 (C-H), 1630 (NC=O), 715 aromatic mono-substitution) $cm^{-1}$. $^1H$ NMR ($DCCl_3$) δ0.11 [d, 2 H, cyclopropyl $CH_{2(ax)}$], 0.49 [t, 2 H, cyclopropyl $CH_{2(eq)}$], 0.92 [m, 2 H, cyclopropyl C-H], 1.74 [m, 3 H, H(5,9)1, 1.98 [bs, 2 H, H(1), $CH_2$ cyclopropyl], 2.23 [bs, 3 H, $H(4,6)_{(ax)}$, $CH_2$ cyclopropyl], 2.94 [d, 1 H, H(6)$_{(eq)}$], 3.01 [d, 1 H, H(2)$_{(ax)}$], 3.28 [m, 2 H, H(8)$_{(ax)}$, H(4)$_{(eq)}$], 3.78 [d, 1 H, H(8)$_{(eq)}$], 4.79 [d, 1 H, H(2)$_{(eq)}$], 7.38 [m, 5 H, Ar-H]; $^{13}$C NMR (DCCl$_3$) ppm 2.85, 4.11 [ cyclopropyl CH$_2$], 7.95 [cyclopropyl C-H], 28.64, 29.01 [(C(1,5)], 31.72 [C(9)], 46.02 [ C(2)], 51.74 [C(8)], 57.71, 57.98 {C( 4,6)], 63.68 [CH$_2$ cyclopropyl], 126.13, 127.64, 128.07, 137.20 [Ar-C], 169.68 [NC=O].

A flask was equipped with a magnetic stirrer and an ice bath. To a chilled (5° C.) solution of the amide 60 (7.15 g, 25.14 mmol) in dry ether (120 ml) was added dropwise HClO$_4$ (60%, 5.26 g, 31.43 mmol) over a 10-min period followed by stirring for an additional 10-min. Filtered salt 12 (a white solid) was washed with dry, cold ether. The white solid was recrystallized (methanol). Filtration and drying afforded 6.30 g (65.1%) of pure salt 12; mp 236.0°–237.0° C. IR (KBr) 3150 (N-H), 3020 (Ar-H), 2880 (C-H), 2840, 1630 (NC=O), 1095 (Cl-O) cm$^{-1}$; $^1$H NMR (DMSO-d$_6$) δ0.47 (bd, 2 H, CH$_{2ax}$ cyclopropyl), 0.71 (d, 2 H, CH$_{2eq}$ cyclopropyl), 1.16 (m, 1 H, C-H cyclopropyl), 1.81 [dd, 2 H, H(9)], 2.28 [bs, 2 H, H(1,5)], 3.32–2.97 (m, 8 H, ring protons, NCH$_2$ cyclopropyl), 3.66 (bd, 2 H, ring protons), 7.95 (m, 5 H, Ar-H); $^{13}$C NMR (DMSO-d$_6$) ppm 5.27 (C-H cyclopropyl), 26.45, 27.66, 62,56 (ring carbons), 126.95, 128.22, 129.33, 136.08 (Ar-C), 172.69 (NC=O). Mass spectral (El) data for C$_{18}$H$_{25}$ClN$_2$O$_5$ m/e (M$^+$): 284.1888 (—HClO$_4$). Found: 284.1888. Anal. Calcd for C$_{18}$H$_{25}$ClN$_2$O$_5$: C, 56.18; H, 6.55. Found: C, 55.92; H, 6.57.

EXAMPLE XIV

7-Benzyl-3-cyclopropylmethyl-3,7-diazabicyclo-[3.3.1]nonane Hydroperchlorate (13) and
7-Benzyl-3-cyclopropylmethyl-3,7-diazabicyclo-[3.3.1]nonane (61)

A jacketed flask was equipped with a magnetic stirrer, a heating mantle, a condensor, a lower takeoff condensor with N$_2$ inlet, and two glass stoppers. To a solution of ketone 48 (9.53 g, 33.51 mmol) in triethylene glycol (100 ml) was added KOH pellets (85%, 17.7 g, 268.08 mmol) and hydrazine (95%, 4.52 g, 134.04 mmol). The stirred mixture was heated at 160°–170° C. for 4 h under N$_2$ via the use of boiling tetralin in the jacket. Cooling the solution to RT was followed by addition of chilled H$_2$O (100 ml). Combined extracts (ether, 4×80 ml) of the suspension were first washed with 10% NaOH (80 ml) and saturated NaCl (80 ml) and then dried (Na$_2$SO$_4$). Filtration and concentration gave a light yellow oil 61 (8.99 g, 98.2%) which was placed under vacuum. The oil 61 gave the following spectral data. IR (film) 3090, 3010, 3005 (ArH), 2920, 2780 (C-H), 735, 700 (C-H out of plane, mono) cm$^{-1}$; $^1$H NMR (DCCl$_3$) δ0.14 [m, 2 H, (CH$_2$)$_{ax}$, cyclopropyl ring], 0.51 [m, 2 H, (CH$_2$)$_{eq}$, cyclopropyl ring], 0.94 [m, 1 H, (CH) cyclopropyl ring], 1.52 [dd, J= 19.8 Hz, 2 H, H(9)], 1.91 [m, 2 H, H(1,5)], 2.20 (d, J = 6.6 Hz, 2 H, CH$_2$-cyclopropyl), 2.33 [dd, J= 10.7 Hz, J=3.6 Hz, 2 H, H(6,8)$_{ax}$], 2.41 [dd, J=10.8 Hz, J= 4.8 Hz, 2 H, H(2,4)$_{ax}$], 2.76 [d, J=10.5 Hz, 2 H, H(6,8)$_{eq}$], 2.85 [d, J=10.5 Hz, 2 H, H(2,4)eq], 3.49 (s, 2 H, Ar-CH$_2$), 7.21–7.45 (m, 5 H, Ar-H); $^{13}$C NMR (DCCl$_3$) ppm 3.90 (CH$_2$, cyclopropyl ring), 8.72 (CH, cyclopropyl ring), 29.43 [C(9)], 30.22 [C(1,5)], 57.68 [C(2,4), 57.90 [C(6,8)], 62.75 (Ar-CH$_2$), 64.04 (CH$_2$-cyclopropyl), 126.38, 127.92, 128.62, 139.74 (Ar-C). Spectral analysis showed no carbonyl group in the IR or C-13 NMR spectrum, and thus this oil 61 was used without further purification to prepare salt 13.

A flask was equipped with a magnetic stirrer and an ice bath. To a chilled (5° C.) solution of amine 61 (4.41 g, 16.31 mmol) in dry ether (150 ml) was added HClO$_4$ (60%, 3.41 g, 20.39 mmol) dropwise over a period of 15 min. The mixture was allowed to stir an additional 15 min at 0°–5° C. A white precipitate formed and was filtered and washed with cold ether. The solid was recrystallized (methanol), and white needles were collected and washed (cold methanol, 25 mi) and dried (Abderhalden, 80° C./0.2 mm Hg, 12 h) to give 4.3 g (71.1%) of salt 13; mp 190°–191° C. IR (KBr) 3060, 3005 (ArH), 2910 2820 (C-H), 1100 (Cl-O), 735, 710 (C-H out of plane, mono) cm$^{-1}$. $^1$H NMR (DMSO-d$_6$) δ 0.46 [m, 2 H, (CH$_2$)$_{ax}$, cyclopropyl ring], 0.62 [m, 2 H, (CH$_2$)$_{eq}$, cyclopropyl ring], 1.07 [m, 1 H, (CH), cyclopropyl ring], 1.64 [d, J= 11.4 Hz, 1 H, H(9)$_{ax}$], 1.77 [d, J= 11.4 Hz, 1 H, H(9)$_{eq}$], 2.42[d, J= 11.1 Hz, 2 H, H(6,8)$_{ax}$], 2.85 (d, J=7.2 Hz, 2 H, CH$_2$-cyclopropyl), 3.09 [m, 4 H, H(2,4)$_{ax}$, H(6, 8)$_{eq}$], 3.54 [bs, 4 H, CH$_2$-Ar, H(2,4)$_{eq}$], 7.31–7.43 (m, 5 H, Ar-H); $^{13}$C NMR (DMSO-d$_6$) ppm 3.87 (CH$_2$, cyclopropyl ring), 6.07 (CH, cyclopropyl ring), 27.46 [C(6)], 29.58 [C(1,5)], 57.01, 56.84 [C(2,4,6,8)], 60.56 (CH$_2$-Ar), 61.49 (CH$_2$-cyclopropyl), 127.57, 128.39, 129.32, 136.49 (Ar-C). Mass spectral (EI) data calcd for C$_{18}$H$_{27}$ClN$_2$O$_4$ m/e (M$^+$): 270.2096 (—HClO$_4$). Found: 270.2093. Anal. Calcd for C$_{18}$H$_{27}$ClN$_2$O$_4$: C, 58.29; H, 7.34. Found: C, 58.39; H, 7.30.

EXAMPLE XV 3-(4-Chlorobenzoyl)-7-cyclopropylmethyl-3,7-diazabicyclo[3.3.1]nonane Hydroperchlorate (14)
and
3-(4-Chlorobenzoyl)-7-cyclopropylmethyl-3,7-diazabicyclo[3.3.1]nonane (62)

A flask was equipped with a magnetic stirrer, a condensor with N$_2$ inlet, an addition funnel, and two glass stoppers. To a mixture of amine 106 (4.03 g, 22.35 mmol) in H$_2$CCl$_2$ (25 ml) and 10% NaOH (22.41 g, 55.88 mmol) was added dropwise a solution of 4-chlorobenzoyl chloride (4.30 g, 24.59 mmol) in H$_2$CCl$_2$ (15 ml) over a period of 30 min. Stirring of the mixture was continued for an additional 3 h under N$_2$. To the heterogenous mixture was added H$_2$O (100 ml) and two layers separated. Further extracts (H$_2$CCl$_2$, 3×50 ml) of the aqueous layer were combined, dried (Na$_2$SO$_4$), filtered and concentrated to give a viscous yellow oil. Flash chromatography of the oil was performed on neutral alumina (50 g) using hexane:ethyl acetate (60:40) as the eluent. The filtrate was concentrated and then placed under vacuum to give 4.18 g (83.1%) of off-white solid 62; mp 67°–68° C. IR (KBr) 3090, 3005 (ArH), 2920, 2880, 2770 (C-H), 1635 (NC=O), 760 (C-H out fo plane, para) cm$^{-1}$. $^1$H NMR (DCCl$_3$) δ 0.12 [m, 2 H, (CH$_2$)$_{ax}$, cyclopropyl ring], 0.54 [m, 2 H, (CH$_2$)$_{eq}$, cyclopropyl ring], 0.91 [m, 1 H, (CH), cyclopropyl ring], 1.73 [m, 3 H, H(5), H(9)], 2.02 [m, 2 H, H(1), CH$_2$-cyclopropyl], 2.24 [m, 3 H, H(4)$_{ax}$, H(6)$_{ax}$, CH$_2$-cyclopropyl], 2.96 [d, J= 10.5 Hz, 1 H, H(6)$_{eq}$], 3.03 [d, J= 13.2 Hz, 1 H, H(2)$_{ax}$], 3.28 [m, 2 H, H(8)$_{ax}$, H(4)$_{eq}$], 3.75 [d, J=13.2 Hz, 1 H, H(8)$_{eq}$] 4.83 [d, J=13.2 Hz, 1 H, H(2)$_{eq}$], 7.39 (s, 4 H, Ar-H); $^{13}$C NMR (DCCl$_3$) ppm 3.21, 4.43 (CH$_2$, cyclopropyl), 8.29 (CH,cyclopropyl), 29.01 [C(1)], 29.41 [ C(5)], 32.10 [C(9)], 46.59 [C(2)], 52.16 [C(8)], 58.10 [C(4)], 58.38 [C(6)], 64.25 (CH$_2$-cyclopropyl), 128.15, 128.28, 134.40, 135.90 (Ar-C), 169.06 (NC=O). Mass spectra (El) data calcd for C$_{18}$H$_{23}$ClN$_2$O m/e (M$^+$): 318.1499. Found: 318.1498. Anal. Calcd for C$_{18}$H$_{23}$ClN$_2$O: C, 67.81; H, 7.27; N, 8.79. Found: C, 67.53; H, 7.25; N, 8.72.

To a flask HClO$_4$ (60%, 0.66 g, 3.92 mmol) was added dropwise to a chilled (5° C.) solution of amide 62 (1.0 g, 3.14 mmol) in ether over a 5 minute period. The resulting precipitate was filtered and washed with cold ether. Recrystallization (methanol) followed by filtration and drying afforded 1.02 g (77.1%) of salt 14 as white needles; mp 231°–232° C. IR (KBr) 3180 (N-H), 3095, 3020 (Ar-H), 2950, 2880 (C-H), 1620 (NC=O), 1090 (Cl-O) cm$^{-1}$; $^1$H NMR (D$_3$C-C≡N) δ0.51 [d, 2 H, cyclopropyl CH$_{2(ax)}$], 0.82 [d, 2 H, cyclopropyl CH$_{2(eq)}$], 1.18 [m, 1 H, cyclopropyl C-H], 1.85 [d, 1 H, H(9)], 2.33 lbs, 3 H, H(1,5,9)], 3.03 [d, 2 H, CH$_2$ cyclopropyl], 3.29 [m, 4 H, ring protons], 3.74 (bs, 2 H, ring protons], 4.09 [bs, 2 H, ring protons], 7.36 [d, 2 H, Ar-H], 7.48 [d, 2 H, Ar-H]; $^{13}$C NMR (D$_3$CC≡N) ppm 4.94, 6.40 [cyclopropyl CH$_2$], 27.89 [C(1,5)], 29.05 [C(9)], 57.42, 63.98, 64.08 [ring carbons], 118.37, 129.67, 129.79, 129.95, 135.08, 136.29 [Ar-C], 173.85 [NC=O). Anal. Calcd for C$_{18}$H$_{24}$N$_2$O$_5$Cl$_2$: C, 51.56; H, 5.77. Found: C, 51.34; H, 5.85.

EXAMPLE XVI

7-Benzyl-3-cyclopropylmethyl-9,9-(1,3-dithiolan-2-yl)-3,7-diazabicyclo[3.3.1]nonane Hydroperchlorate (15) and 7-Benzyl-3-cyclopropylmethyl-9,9-(1,3-dithiolan-2-yl)-3,7-diazabicyclo[3.3.1]nonane (112)

A flask was equipped with a magnetic stirrer, condensor with a N$_2$ inlet, a Dean-Stark trap, and a heating mantle. After addition of the ketone 48 (6.0 g, 21.09 mmol), 1,2-ethanedithiol (19.87 g, 210.9 mmol), p-toluenesulfonic acid (9.63 g, 50.6 mmol) and benzene (120 ml) were added, and the resulting mixture was heated at reflux for 30 h. The solvent was removed through a Dean-Stark trap and the resulting oil was dissolved in H$_2$O (100 ml). The aqueous layer was extracted (ether, 2×50 ml) and the extracts were discarded. Basification of the aqueous solution (pH~12) was achieved using an aqueous 10% NaOH solution. This new solution was extracted (ether, 4×75 ml) and the extracts were then washed with NaOH (1 N, 90 ml) and saturated NaCl (90 ml). After drying (Na$_2$SO$_4$), the organic solution was evaporated to afford 6.44 g (84.7%) of 112, a light yellow oil; IR (film) 3080, 3010, 3000 (ArH), 2905, 2800 (C-H), 730, 705 (C-H out of plane, mono) cm$^{-1}$; $^1$H NMR (DCCl$_3$) δ0.14 [m, 2 H, (CH$_2$)$_{ax}$, cyclopropyl ring], 0.51 [m, 2 H, (CH$_2$)$_{eq}$, cyclopropyl ring], 0.92 [m, 1 H, (CH), cyclopropyl ring], 2.15 [m, 2 H, H(1,5)], 2.27 (d, 2 H, CH$_2$-cyclopropyl), 2.73–2.84 (m, 8 H, ring protons), 3.14 (s, 4 H, SCH$_2$), 3.53 (s, 2 H, Ar-CH$_2$), 7.24–7.46 (m, 5 H, Ar-H); $^{13}$C NMR (DCCl$_3$) ppm 3.83 (CH$_2$, cyclopropyl ring), 8.60 (CH, cyclopropyl ring), 37.93, 37.98 [C(1,5)], 43.51 (SCH$_2$), 56.56 [C(2,4)], 56.67 [C(6,8)], 61.68 (CH$_2$-Ar), 62.49 (CH$_2$-cyclopropyl), 71.91 [C(9)], 126.60, 128.02, 128.62, 139.34 (Ar-C). Thioketal 112 was used without further purification to prepare salt 15.

Into a flask equipped with a magnetic stirrer and an ice bath was placed thioketal 112 (6.44 g, 17.86 mmol) in dry ether (100 ml), and the solution was cooled to 0°–5° C. To the stirred mixture was added dropwise perchloric acid (60%, 3.73 g, 22.32 mmol) over a period of 15 min. After stirring an additional 15 min at 5° C., a white precipitate was filtered and washed with cold ether (25 ml). Recrystallization (methanol) and drying afforded hydroperchlorate 15 as white needles (3.34 g, 40.6%); m.p. 147.5°–149.0° C. IR (KBr) 3090, 3010 (ArH), 2940, 2850 (C-H), 1100 (Cl-O), 735, 705 (C-H out of plane, mono) cm$^{-1}$. $^1$H NMR (DCCl$_3$) δ0.59 [m, 2 H, (CH2)$_{ax}$, cyclopropyl ring], 0.68 [m, 2 H, (CH$_2$)$_{eq}$, cyclopropyl], 0.98 [m, 1 H, (CH) cyclopropyl ring], 2.26 [bs, 2 H, H(1,5)], 3.01 [m, 4 H, H(2,4)$_{ax}$, CH$_2$-cyclopropyl], 3.31–3.46 [m, 8 H, H(6,8)$_{ax}$, H(2,4)$_{eq}$, SCH$_2$], 3.73 (s, 2 H, Ar-CH$_2$). 3.92 [dd, 2 H, H(6,8)$_{eq}$], 7.28–7.45 (m, 5 H, Ar-H); $^{13}$C NMR (DCCl$_3$) ppm 4.29 (CH$_2$, cyclopropyl ring), 6.10 (CH, cyclopropyl ring), 39.19, 39.35 (SCH$_2$), 41.73 [C(1,5)], 56.12 [C(2,4)], 56.92 [C(6, 8)], 60.96 (Ar-CH2), 60.99 (CH$_2$-cyclopropyl), 69.42 [C(9)], 128.04, 128.57, 129.89, 135.09 (Ar-C). Mass spectra (EI) data calcd for C$_{20}$H$_{29}$ClN$_2$O$_4$S$_2$ m/e (M+): 360.1694 (—HClO$_4$). Found: 0.1703. Anal. Calcd. for C$_{20}$H$_{29}$ClN$_2$O$_4$S$_2$: C, 52.10; H, 6.34; N, 6.08; S, 13.91. Found C, 51.98; H, 6.30; N, 5.81; S, 14.05.

EXAMPLE XVII

7-Benzyl-3-cyclopropylmethyl-3,7-diazabicyclo-[3.3.1]nonan-9-one (48)

A flask was equipped with a magnetic stirrer, a heating mantle, an addition funnel, a condensor with N$_2$ inlet, and a glass stopper. A mixture of cyclopropylmethylamine (4.44 g, 62.4 mmol), HCl (37%, 3.07 g, 31.2 mmol), glacial acetic acid (3.75 g, 62.4 mmol) and parformaldehyde (3.94 g, 131.04 mmol) in deoxygenated (N$_2$ bubbled in for 2 h) methanol (125 ml) was stirred at reflux for 15 min under N$_2$. A solution of N-benzyl-4-piperidinone (102, 11.8 g, 62.4 mmol) and glacial acetic acid (3.75 g, 62.4 mmol) was added dropwise over a period of 1.5 h. After 10 h at reflux, the mixture was treated with additional paraformaldehyde (3.94 g, 131.04 mmol) in one portion. Heating at reflux was continued for another 19 h. Upon cooling to RT, concentration of the solution gave an orange oil which was redissolved in H$_2$O (100 ml). Extracts (ether, 2×75 ml) of the aqueous solution were discarded. The aqueous layer was chilled (5° C.) and then made basic (pH~12) with NaOH pellets. Extraction (H$_2$CCl$_2$, 3× 75 ml) gave a solution which was dried (Na$_2$SO$_4$), filtered, and concentrated to a viscous, reddish-orange oil. Distillation of the oil under reduced pressure (175–190C/10$^{-5}$ mm Hg) gave 13.54 g (76.3%) of a light yellow oil which solidified upon standing at –10° C.; mp 56.0°–57.5° C. This solid was recrystallized (pentane) to give an analytical sample of 48; mp 58.5°–59.5° C. IR (KBr) 3090, 3070, 3030 (Ar-H), 3005 (C-H, cyclopropyl), 2975, 2910, 2830 (C-H), 1740 (C=O), 1600, 1495 (ArC=C), 740, 710 (C-H out of plane, mono) cm$^{-1}$; $^1$H NMR (DCCl$_3$) δ0.12 [dq, 2 H, (C-H)$_{ax}$, cyclopropyl ring], 0.51 [dq, 2 H (C-H)$_{eq}$, cyclopropyl ring], 0.89 [m, 1 H, (C-H), cyclopropyl ring], 2.32 (d, 2 H, CH$_2$-cyclopropyl), 2.59 [m, 2 H, H(1,5)], 2.81 [dd, J= 10.8 Hz, J=5.6 Hz, 2 H, H(6,8)$_{ax}$], 2.94 [dd, J= 10.8 Hz, J=6.8 Hz, 2 H, H(2,4)$_{ax}$], 3.04 [dd, J=10.8 Hz, J=3.2 Hz, 2 H, H( 6.8)$_{eq}$], 3.12 [dd, J= 10.8 Hz, J= 3.2 Hz, 2 H, H(2,4)eq], 3.57 (s, 2 H, CH$_2$Ph), 7.38–7.22 (m, 5 H, Ar-H), $^{13}$C NMR (DCCl$_3$) ppm 3.76 (CH$_2$, cyclopropyl ring), 8.53 (CH, cyclopropyl ring), 46.76 [C(1,5)], 58.19 [C(2,4)], 58.36 [C(6,8)], 61.11 (CH$_2$Ph), 61.85 (CH$_2$-cyclopropyl), 127.08, 128.22, 128.66, 138.54 (Ar-C), 214.85 [C=O]; $^{15}$N NMR (DCCl$_3$) ppm 36.17 [N(7)], 37.74 [N(3)]; Mass spectral (EI) data calcd for C$_{18}$H$_{24}$N$_2$O m/e(M+): 284.1188; Found: 284.1190. Anal. Calcd for C$_{18}$H$_{24}$N$_2$O: C, 76.02; H, 8.51; N, 9.85. Found: C, 76.19; H, 8.46; N, 9.99.

EXAMPLE XVIII

3,7-Diisopropyl-3,7-diazabicyclo[3.3.1]nonan-9-one (47)

A flask was equipped with a magnetic stirrer, a heating mantle, an addition funnel a condensor with N$_2$ inlet and a glass stopper. A mixture of isopropylamine (8.87 g, 150.0 mmol) HCl (37%, 7.39 g, 75.0 mmol), glacial acetic acid (9.01 g, 150.0 mmol) and parformaldehyde (9.46 g, 315.0 mmol) in deoxygenated ($N_2$ bubbled in for 2 h) methanol (125 ml) was stirred at reflux for 15 min under $N_2$. A solution of N-isopropyl-4-piperidinone (101, 21.18 g, 150.0 mmol) and glacial acetic acid (9.01 g, 150.0 mmol) was added dropwise over a period of 1.5 h, which was followed by a period of boiling for an additional 23 h. After the initial 10 h of heating, paraformaldehyde (9.46 g, 315.0 mmol) was added in one portion to the mixture. Concentration of the solution (after 23 h) gave an orange oil which was redissolved in $H_2O$ (150 ml), and extracts (ether, 2×100 ml) thereof were discarded. The aqueous layer was chilled (5° C.) in an ice bath and made basic (pH~12) with NaOH pellets. Extraction ($H_2CCl_2$, 3×75 ml) gave a solution which was dried ($Na_2SO_4$), filtered, and concentrated to give a viscous, reddish-orange oil. Distillation of the oil under reduced pressure (110°–120° C./$10^{-5}$ mm Hg) gave 22.53 g (67.3% of a light yellow oil 47. IR (film) 2975, 2910, 2830 (C-H), 1735 (C=O) cm$^{-1}$. $^1$H NMR (DCCl$_3$) δ 1.02 (d, 12 H, CH$_3$ isopropyl), 2.58 [m, 2 H, H(1,5)], 2.87 [m, 6 H, H(2,4,6,8)$_{ax}$, C-H isopropyl], 3.04 [dd, 4 H, H(2,4,6,8)$_{eq}$]; $^{13}$C NMR (DCCl$_3$) ppm 17.9, 18.2 (CH$_3$, isopropyl), 46.82 C(1.5), 53.17 (C-H isopropyl), 53.27, 53.36 C(2,4,6,8), 215 C(9). Anal. Calcd for C$_{13}$H$_{24}$N$_2$O: C, 69.59; H, 10.78; N, 12.49. Found: C, 69.39; H, 10.61; N, 12.21.

EXAMPLE XIX

3-Cyclopropylmethyl-3,7-diazabicyclo[3.3.1]nonane (106)

A flask was equipped with a magnetic stirrer, a heating mantle, a condensor with $N_2$ inlet, and two glass stoppers. The flask was initially flushed with $N_2$ for a period of 15 min. Palladium-on-carbon (10%, 0.997 g, 30 mg of catalyst/mmol of the amine) was added in one portion, and the system was flushed with $N_2$. Dry and deoxygenated CH$_3$OH was slowly poured over the catalyst (CAUTION: catalyst can ignite in presence of air). To the stirred solution were added amine 61 (8.99 g, 33.24 mmol) and anhydrous HCO$_2$NH$_4$ (5.24 g, 83.1 mmol), and the resulting mixture was boiled under $N_2$ for 30 min. Cooling the mixture to RT, and filtering through a celite pad, was followed by concentration of the resulting solution to give an off-white, viscous oil. The oil was then dissolved in $H_2O$ and made basic (pH~12) using 10% NaOH. Combined extracts (CCl$_4$, 4×60 ml) of the aqueous solution were dried (Na$_2$SO$_4$), filtered and concentrated to give a yellow oil 106 (5.50 g, 91.8%); IR (film) 3300 (N-H), 3090, 3010 (CH$_2$ cyclopropyl), 2900, 2860, 2780 (C-H) cm$^{-1}$; $^1$H NMR (DCCl$_3$) δ0.13 [m, 2 H, (CH$_2$)$_{ax}$, cyclopropyl ring], 0.52 [m, 2 H, (CH$_2$)$_{eq}$, cyclopropyl ring], 0.87 [m, 1 H, (CH), cyclopropyl ring], 1.64 [m, 2 H, H(1,5)], 1.82 [md, 2 H, H(9)], 2.07 (d, J= 6.6 Hz, 2 H, CH$_2$-cyclopropyl), 2.31 [td, J= 11.1 Hz, 2 H, H(6,8)$_{ax}$], 2.94 [td, J= 13.8 Hz, 2 H, H(2,4)$_{ax}$], 3.09 [ d, J=13.2 Hz, 2 H, H(6,8)$_{eq}$], 3.17 [d, J= 11.1 Hz, 2 H, H(2,4)$_{eq}$], 4.09 [bs, 1 H, (N-H)]; $^{13}$C NMR (DCCl$_3$) ppm 3.76 (CH$_2$, cyclopropyl ring), 8.76 (CH, cyclopropyl ring), 29.87 [C(9)], 33.23 [C(1,5)], 52.45 [C(6.8)], 59.51 [C(2,4)], 64.32 (CH$_2$-cyclopropyl). NMR data showed the absence of the benzyllic group, and thus 106 was used without further purification to prepare amides 60 and 62 and their hydroperchlorates 12 and 14, respectively.

EXAMPLE XX

7-Benzyl-3-thia-7-azabicyclo[3.3.1]nonane Hydrochloride (113)

This amine salt was prepared by the general method outlined in U.S. Pat. No. 4,581,361

EXAMPLE XXI

3-[4-(Nitro)phenylacetyl]-7-isopropyl-3,7-diazabicyclo[3.3.1]nonane (94)

A standard setup was used with a $N_2$ inlet. Initially, the amine 105 (2.42 g, 14.38 mmol) in $H_2CCl_2$ (35 ml) was added followed by NaOH (10%, 14.42 g, 35.95 mmol) which resulted in a heterogenous mixture. To this mixture was added 4-nitrophenylacetyl chloride (3,16 g, 15.82 mmol) dropwise over a 15-min period. Stirring was continued for an additional 3 h upon which the brown mixture was transferred to a separatory funnel, and the layers were separated. The aqueous layer was extracted ($H_2CCl_2$, 3×25 ml), and the organic layers were combined. After drying (Na$_2$SO$_4$, 2 h), the organic solution was filtered and concentrated to give 94 as a light brown solid (3.3 g, 69.2 %); mp 93°–94°]C. IR (KBr) 3090 (Ar-H), 2960, 2920, 2800, 2740 (C-H), 1625 (NC=O) cm$^{-1}$; $^1$H NMR (DCCl$_3$) d 0.94 (dd, 6 H, CH$_3$ isopropyl), 1.69 [q, 2 H, H(9)], 1.92 [bs, 2 H, H(1,5)], 2.46 [m, 3H, ring protons, C-H, isopropyl), 2.79 (d, 1 H, ring proton), 2.93 (td, 2 H, ring protons), 3.39 (d, 1 H, ring proton), 3.79 (s, 2 H, CH$_2$-Ar), 3.84 (d, 1 H, ring proton), 4.57 (d, 1 H, ring proton), 7.44 (d, 2 H; Ar-H), 8.15 (d, 2 H, Ar-H); $^{13}$C NMR (DCCl$_3$) ppm 16.83, 18.44 (CH$_3$ isopropyl), 28.76, 29.42 [C(1,5)1, 31.57 [C(9)], 40.62 (CH$_2$-Ar), 46.76 (C-H isopropyl), 50.60, 52.78, 54.03, 54.42 [C(2,4,6,8)], 123.37, 130.02, 143.58, 146.56 (Ar-C), 167.93 (NC=O). Amide 94 was used without further purification.

EXAMPLE XXII

3-[4-(Nitro)phenylacetyl]-7-isopropyl-3,7-diazabicyclo[3.3.1]nonane Hydroperchlorate (95)

A solution of amide 94 (0.55 g, 1.66 mmol) in ether (40 ml) contained in a flask equipped with a ice bath and a magnetic stirrer was chilled (5° C.) with stirring. Upon dropwise addition of HClO$_4$ (60%, 0.35 g, 2.07 mmol) a white precipitate resulted which was allowed to stir for 15 min at this temperature. After filtering, the solid was recrystallized (minimum amount of hot H$_3$COH-20 ml), filtered, and allowed to stand at room temperature. This new solid was filtered (suction) and dried (Abderhalden, 80° C./7 mm Hg) to give 0.52 g (72.6%) of salt 95; mp 225°–226° C. IR (KBr) 3160 (N-H), 3090 (Ar-H), 2980, 2940 2890 (C-H), 1665 (NC=O), 1100 (Cl-O) cm$^{-1}$; $^1$H NMR (D3CCN), d 1.31 (d, 6 H, CH$_3$ isopropyl), 1.82 [d, 1 H, H(9)$_{ax}$], 1.95 [d, 1 H, H(9)$_{eq}$]2.36 [s, 2 H, H(1,5)]3.22 (m, 4 H, rig protons), 3.49 (m, 3 H, ring protons, C-H isopropyl), 3.94 (bs, 2 H, Ar-CH$_2$), 4.18 (bd, 2 H, ring protons), 7.47 (d, 2 H, Ar-H), 8.28 (d, 2 H, Ar-H); $^{13}$C NMR (D$_3$CCN) ppm 16.79 (CH$_3$ isopropyl), 27.79 [C(1,5)], 28.53 [C(9)], 41.09 (Ar-CH$_2$), 48.32, 53.81 [bs, C(2,4,6,8)], 60.95 (C-H isopropyl), 118.33, 124.17, 132.02, 144.58 (Ar-C), 173.96 (NC=O); Anal. Calcd for C$_{18}$H$_{26}$ClN$_3$O$_7$: C, 50.06; H, 6.07. Found: C, 49.76; H, 6.16.

EXAMPLE XXIII

3-[4-(Amino)phenylacetyl]-7-isopropyl-3,7-diazabicyclo[3.3.1]nonane (96)

To a flask equipped with a magnetic stirrer was added amide 94 (5.4 g, 16.3 mmol) in AcOH/H$_2$O (1:1, 80 ml). After obtaining a homogenous solution, TiCl$_3$ (12%, 135.3 g, 114.1 mmol) was added in one portion, and this purple solution stirred at room temperature for 7 min. Upon cooling (ice bath, 5° C.) the reaction mixture, 20% NaOH was added until a dark blue color persisted (pH~12). Extraction (HCCl$_3$, 3×100 ml) was followed by washing of the organic layer with H$_2$O (150 ml) and satd NaCl (150 ml). The organic layer was dried (Na$_2$SO$_4$, 3 h), filtered, and concentrated to give 96 (4.03 g, 82.1%) as a light yellow, viscous oil. IR (film) 3350, 3240 (N-H), 3040 (Ar-H), 2980, 2930, 2800 (C-H), 1630 (NC=O) cm$^{-1}$; $^1$H NMR (DCCl$_3$) d 0.93 (dd, 6 H, CH$_3$ isopropyl), 1.61 [q, 2 H, H(9)], 1.82 [d, 2 H, H(1,5)], 2.32–2.49 (m, 3 H, ring protons, C-H isopropyl), 2.71 (d, 1 H, ring proton), 2.86 (d, 1 H, ring proton), 2.92 (d, 1 H, ring proton), 3.25 (d, 1 H, ring proton), 3.58 (q, 2 H, Ar-CH$_2$), 3.69 (bs, 2 H, NH$_2$), 3.83 (d, 1 H, ring proton), 4.51 (d, 1 H, ring proton), 6.58 (d, 2 H, Ar-H), 7.01 (d, 2 H, Ar-H); $^{13}$C NMR (DCCl$_3$) ppm 16.48, 18.06 (CH$_3$ isopropyl), 28.46, 29.01 [C(1,5)], 31.15 [C(9)], 40.20 (Ar-CH$_2$), 46.14 (C-H isopropyl), 50.13, 52.52, 53.51, 53.89 [C(2,4,6,8)], 114.75, 125.58, 129.04, 144.71 (Ar-C), 169.80 (NC=O). Amine 96 was used directly without further purification to prepare sulfonamide 97.

EXAMPLE XXIV

3-[4-(Methylsulfonyl)amino]phenylacetyl-7-isopropyl-3,7-diazabicyclo[3.3.1]nonane (97)

A standard setup was equipped with a N$_2$ inlet. To a chilled (5° C.) solution of amide 96 (2.1 g, 6.97 mmol) and pyridine (0.58 g, 7.32 mmol) in H$_2$CCl$_2$ (20 ml) was added dropwise methanesulfonyl chloride (0.79 g, 6.90 mmol) in H$_2$CCl$_2$ (10 ml) over a 15 min period. After the addition was complete, the mixture stirred at RT overnight. Filtration of the mixture removed traces of pyridine hydrochloride, and the filtrate was transferred to a separatory funnel. Extraction (1 N NaOH, 4×40 ml) was followed by neutralization (pH~7) of the aqueous phase using acetic acid, and the remaining organic layer was discarded. This neutral solution was extracted (H$_2$CCl$_2$, 4×40 ml), dried (Na$_2$SO$_4$, 2 h) and filtered. After concentration, sulfonamide 97 was obtained 2.32 g (87.4%) as an off-white solid; mp 73°–74° C. IR (KBr) 3140 (N-H), 3050 (Ar-H), 2980, 2920, 2880, 2800 (C-H), 1630 (NC=O) cm$^{-1}$; $^1$H NMR (DCCl$_3$) d 0.94 (dd, 6 H, CH$_3$ isopropyl), 1.69 [dd, 2 H, H(9)], 1.93 [bs, 2 H, H(1,5)], 2.41 (d, 1 H, ring proton), 2.52 (m, 2 H, ring proton, C-H isopropyl), 2.84 (d, 1 H, ring proton), 2.93 (m, 6 H, ring protons, SO$_2$CH$_3$), 3.38 (d, 1 H, ring proton), 3.66 (s, 2 H, Ar-CH$_2$), 3.90 (d, 1 H, ring proton), 4.59 (d, 1 H, ring proton), 7.11 (dd, 4 H, Ar-H), 7.37 (s, 1 H, SO$_2$N-H); $^{13}$C NMR (DCCl$_3$) ppm 17.17, 18.31 (CH$_3$ isopropyl), 28.84, 29.47 [C(1,5)], 31.62 [C(9)], 38.76 (SO$_2$CH$_3$), 40.05 (Ar-CH$_2$), 46.89 (C-H isopropyl), 50.58, 53.04, 54.07, 54.30 [C(2,4,6,8)], 121.66, 130.13, 132.44, 135.68 (Ar-C), 169.77 (NC=O). Amide 97 was used without further purification to prepare hydroperchlorate 98.

EXAMPLE XXV

3-[4-(Methylsulfonyl)amino]phenylacetyl-7-isopropyl-3,7-diazabicyclo[3.3.1]nonane Hydroperchlorate (98)

To a flask equipped with a magnetic stirrer and an ice bath was added sulfonamide 97 (1.73 g, 4.56 mmol) dissolved in H$_3$COH/ether 1:1, 40 ml), and the resulting solution was chilled (5° C.). With stirring, HClO$_4$ (60%, 0.95 g, 5.70 mmol) was added dropwise over a period of 15 min and stirring was continued an additional 10 min at this temperature. The white precipitate was filtered and recrystallized (hot H$_3$COH-25 ml)to give 1.54 g (70.7%) of 98 as white platelettes; mp 177:5°–178.5° C. IR (KBr) 3250 (N-H), 3160 (N-H), 3020 (Ar-H), 2940, 2920, 2860 (C-H), 1665 (NC=O), 1100 (Cl-O) cm$^{-1}$; $^1$H NMR (D$_3$CCN) d 1.28 (d, 6 H, CH$_3$ isopropyl), 1.79 [d, 1 H, H(9)$_{ax}$], 1.92 [d, 1 H, H(9)$_{eq}$], 2.33 [bs, 2 H, H(1,5)], 2.96 (s, 3 H, SO$_2$CH$_3$), 3.11–3.28 (m, 4 H, ring protons), 3.44 (m, 3 H, ring protons, C-H isopropyl), 3.78 (bs, 2 H, Ar-CH$_2$), 4.19 (d, 2 H, ring protons), 6.58 (bs, 1 H, N-H), 7.23 (m, 4 H, Ar-H), 7.60 (s, 1 H, SO$_2$ N-H); $^{13}$C NMR (D$_3$CCN) ppm 16.67 (bs, CH$_3$ isopropyl), 27.79 [C(1,5)], 28.55 [C(9)1, 39.56 (SO$_2$CH$_3$), 40.86 (Ar-CH$_2$), 48.30, 53.80 [ bs, C(2,4,6,8)], 60.88 (C-H isopropyl), 121.93, 131.56, 132.88, 137.38 (Ar-C), 174.94 (NC=O). Anal. Calcd for C$_{19}$H$_{30}$ClN$_3$O$_7$S: C, 47.55; H, 6.30. Anal. Calcd for C$_{19}$H$_{30}$ClN$_3$O$_7$S.0.4 H$_2$O: C, 46.84; H, 6.37. Found: C, 46.55; H, 6.26.

EXAMPLE XXVI

3-[4-(N-acetyl)phenylacetyl]-7-isopropyl-3,7-diazabicyclo[3.3.1]nonane (99)

To a standard setup equipped with a with N$_2$ inlet, was added a mixture of amide 96 (2.0 g, 6.63 mmol) in H$_2$CCl$_2$ (25 ml) and 10% NaOH (6.65 g, 16.58 mmol). To this mixture was added dropwise a solution of acetyl chloride (0.57 g, 7.30 mmol) in H$_2$ CCl$_2$ (5 mi) over a period of 15 min. Stirring (magnetic) of the mixture was continued for an additional 3 h under N$_2$. To the heterogenous mixture was added H$_2$O (100 ml) and the two layers were separated. Further extracts (H$_2$CCl$_2$, 3×30 ml) of the aqueous layers were combined and dried (Na$_2$SO$_4$, 1 h), filtered, and concentrated. The resulting oil was placed on a vacuum pump overnight (RT/0.2 mm Hg) to give 2.03 g (89.1%) of 99 as an light yellow solid; mp 71°–72° C. IR (KBr) 3300 (N-H), 3080, 3050 (Ar-H), 2980, 2930, 2870, 2800 (C-H), 1680 [NC(O)CH$_3$], 1620 (NC=O) cm$^{-1}$; $^1$H NMR (DCCl$_3$) d 0.94 (dd, 6 H, CH$_3$ isopropyl), 1.68 [dd 2 H, H(9)], 2.11 [s, 3 H, CH$_3$C(O)], 2,40 (d, 1 H, ring proton), 2.49 (m, 2 H, ring proton, C-H isopropyl), 2.78 (d, 1 H, ring proton), 2.87 (d, 1 H ring proton), 2.96 (d, 1 H, ring proton), 3.32 (d, 1 H, ring proton), 3.64 (d, 2 H, Ar-CH$_2$), 3.87 (d, 1 H, ring proton), 4.55 (d, 1 H, ring proton), 7.08 (d, 2 H, Ar-H), 7.36 (d, 2 H, Ar-H), 8.70 (s, 1 H, N-H); $^{13}$C NMR (DCCl$_3$) ppm 16.99, 18.33 (CH$_3$ isopropyl), 24.13 [CH$_3$C(O)], 28.83, 29.39 [C(1,5)], 31.55 [C(9)], 40.49 (Ar-CH$_2$), 46.75 (C-H isopropyl), 50.62, 53.02, 53.99, 54.28 (Ar-C), 168.89 [NH-C(O)CH$_3$], 169.94 (NC=O). Amide 99 was used directly to prepare hydroperchlorate 100 without further purification.

EXAMPLE XXVII

3-[4-(N-acetyl)phenylacetyl]-7-isopropyl-3,7-diazabicyclo[3.3.1]nonane Hydroperchlorate (100)

A chilled (5° C., via ice bath) solution of amide 99 (2.03 g, 5.91 mmol) in H$_3$COH/ether (50:50, 25 ml) was contained in a flask equipped with a magnetic stirrer. Addition of HClO$_4$ (60%, 0.72 g, 4.30 mmol) dropwise over a period of 5 min was followed by continual stirring at this temperature for an additional 15 min. This precipitate was filtered and washed with cold ether. Recrystallization (H$_3$COH, 35 ml) of the precipitate gave a new solid which was filtered and dried (80° C./0.2 mm Hg, 12 h) to give 1.98 g (75.4%) of salt 100 as white platelettes; mp 197°–198° C. IR (KBr) 3360 (N-H), 3100 (N-H), 3040 (Ar-H), 2940, 2860 (C-H), 1675 [NHC(O)CH$_3$], 1645 (NC=O), 1100 (Cl-O) cm$^{-1}$; $^1$H NMR (D$_3$CCN) d 1.24 (d, 6 H, CH$_3$ isopropyl), 1.78 [d, 1 H, H(9)$_{ax}$], 1.91 [d, 1 H, H(9)$_{eq}$], 2.06 [s, 3 H, NC(O)CH$_3$], 2.29 [bs, 3 H, H(1,5), ring proton], 3.02–3.26 (m, 3 H, ring proton, C-H isopropyl), 3.43 (m, 3 H, ring proton), 3.72 (s, 2 H, Ar-CH$_2$), 4.19 (d, 2 H, ring protons), 7.18 (d, 2 H, Ar-H), 7.51 (d, 2 H, Ar-H), 8.36 (bs, 1 H, CH$_3$C(O)N-H); $^{13}$C NMR (D$_3$CCN) ppm 16.75 (CH$_3$ isopropyl), 24.29 [NC(O)CH$_3$], 27.81 [C(1,5)], 28.60 [C(9)], 41.11 (Ar-CH$_2$), 48.31, 53.95 [bs, C(2,4,6,8)], 60.86 (C-H isopropyl), 120.54, 130.72, 131.16, 138.77 (Ar-C), 169.56 [NH-C(O)CH$_3$ ], 175.01 (NC=O). Anal. Calcd for C$_{20}$H$_{30}$ClN$_3$O$_6$: C, 54.11; H, 6.81. Anal. Calcd for C$_{20}$H$_{30}$ClN$_3$O$_6$·0.8 H$_2$O: C, 52.41; H, 6.95. Found: C, 52.52; H, 6.92.

BIOLOGICAL RESULTS

To illustrate the useful biological properties of the compounds described in this invention, selected derivatives were screened for antiarrhythmic agent (AAA) activity using dog models. A a standard for comparison purposes, we tested the DHBN members described herein against a commonly used antiarrhythmic agent, lidocaine, as well as against 7-benzyl-3-thia-7-azabicyclo[3.3.1]nonane hydroperchlorate (114) [U.S. Pat. No. 4,581,361], and 7-benzyl-3-thia-7-azabicyclo [3.3.1]nonane hydrochloride (113). The results summarized in the Table below show the range of antiarrhythmic activites observed. It should be emphasized that the members of the DBCN have a minimal of proarrhythmic activity which enhances their potential utility. The substituents attached to the DBCN skeleton and described in this document could not be predicted to elicit the remarkable multi-class antiarrhythmic activity observed and with such a low incidence of proarrhythmic activity.

| Antiarrhythmic Properties of Selcted Representative 3,7-Diheterabicylo[3.3.1]nonanes and Derivatives In Dogs with Myocardial Infarctions And Induced Ventricular Tachycardia | |
|---|---|
| Compd$^a$ | Results Observed with SVT 3 mg/kg or 6 mg/kg of Body Weight of the Dog |
| 1 | Increased VERP;$^b$ QT prolonged; Lowered HR$^c$ by 10–30 beats/min; no proarrhythmic action$^d$ (Class I and III AAA$^e$ activity) |
| 2 | Increased VERP;$^b$ QT prolonged; Lowered HR$^c$ by 5–15 beats/min (Class III AAA$^e$ activity) |
| 3 | NSVT$^f$ (SVT$^g$ was abolished); (Class I and III AAA$^e$ activity) |
| 5 | Increased VERP$^b$; QT prolonged 30%, Lowered HR$^c$ by by 20–40 beats/min; prevented SVT$^g$ from being induced in dogs with SVT in a controlled state; no hemodynamic depression; prevented gernation of SVT$^g$; (Class I and III AAA$^e$ activity) |
| 11 | Increased VERP$^b$; QT prolonged; NSVT$^f$ (SVT$^g$ was abolished); slight depression of intraventricular conduction; prevented induction of induced SVT$^g$; (Class I and III AAA$^e$ activity) |
| 12 | Increased RVERP$^h$; QT not prolonged; Lowered HR$^c$ by 10 beats/min; prevented induction of induced SVT$^g$; (Class I and III AAA$^e$ activity) |
| 13 | Lowered HR$^c$; Lowered MBP$^i$; Class II AAA$^e$ activity possible |
| 53 | No influence or QT$_{sinus}$$^j$; No influence on HR$^c$ |
| 62 | Increased RVERP$^h$; QT prolonged; NSVT$^f$ (prevented generation of SVT$^g$); (Class I and II AAA$^e$ activity) |

-continued

| Antiarrhythmic Properties of Selcted Representative 3,7-Diheterabicylo[3.3.1]nonanes and Derivatives In Dogs with Myocardial Infarctions And Induced Ventricular Tachycardia | |
|---|---|
| Compd$^a$ | Results Observed with SVT 3 mg/kg or 6 mg/kg of Body Weight of the Dog |
| 108 | Increased HV$^k$; Increased MBP$^i$; Prevented SVT in some dogs but not in others; (Class I AAA$^e$ activity) |
| 109 | Increased RVERP$^b$; Increased MBP$^i$; Markedly slowed SVT or abolished SVT; highly selective action on ischemically damaged tissue; lack of a negative inotropic action in vitro and in vivo (Class I and Class III AAA$^e$ activity and with very low proarrhythmic action$^d$) |
| Lidocaine | Lowered MBP; showed marked proarrhythmic action in all of the dog models |

$^a$X = ClO$_4$, Cl, Br, HSO$_4$, citrate, fumarate, maleate
$^b$VERP = Ventricular effective refractory period
$^c$HR = Heart rate in beats/minute (bpm)
$^d$Proarrhythmic action means agent increased rate of existing SVT or a new and faster SVT was inducible
$^e$AAA = Antiarrhythmic activity
$^f$NSVT = Nonsustained ventricular tachycardia (or abolished ventricular tachycardia)
$^g$SVT = Sustained ventricular tachycardia induced by programmed electrical pacing of infarcted dog heart
$^h$RVERP = Right ventricular effective refractory period
$^i$MBP = Mean blood pressure
$^j$QT$_{sinus}$ = QT interval during spontaneous rhythm
$^k$HV = HIS Purkinj or intraventricular conduction time The claims and specifications delineated herein describe the invention, and the terms employed draw their meaning from the specifications presented. It is felt that the compositions of the present invention can be utilized individually or in combinations. It is clear from the Table that multi-class action (as defined by the Vaughn-Williams classification method) is present in the compositions in varying degrees. Administration of such compositions can be administered to by way of example, but not limited thereto, intraveneously, orally, by suppository, inhalation, and the like. Moreover, it is also felt that the compositions claimed possess useful antiarrhythmic agent (AAA) activity or generally are broadly biologically active or the respective composition are intermediates to useful anatiarrhythmic or biologically active species that are released or generated in situ as a result of administration of the composition. Descriptions of the dog models employed can be found in U.S. Pat. Nos. 4,581,361; 4,778,892; 4,910,311; 4,980,468; 5,043,445; 5.084,572; and 5,110,933. Technology for determining class activity can be found in "Electrophysiological Actions of BRB-I-28 in Canine Myocardiai Tissues", by E. Patteson, B. J. Scherlag, K. D. Berlin, and R. Lazzara in The Journal of Pharmacology and Experimental Therapeutics, volume 259, pages 558–656 (1991) and in "Comparative Electrophysiological and Hemodynamic Actions of BRB-I-28 and Lidocaine in the Normal and Infarcted Dog Heart:, by B. J. Scherlag, E. Patterson, R. Lazzara, B. R. Bailey, Jr., M. D. Thompson, and K. D. Berlin in the Journal of Electrophysiology, volume 2, pages 461–477 (1988).

Having thus described and exampified the preferred embodiments with a degree of particularity, it is understood that the invention is not limited to the embodiments set forth herein for the purposes of exemplification, but it limited to the scope of the attached claims, including the full range of equivalency to which each element thereof is entitled.

We claim:

1. 3-Alkyl-7-substituted -3-azabicyclo[3.3.1]nonan-9-ones characterized by the formula:

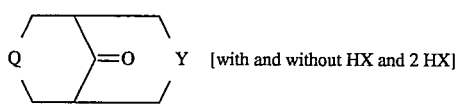  [with and without HX and 2 HX]

X=ClO$_4$, Cl, Br, HSO$_4$, citrate, fumarate, or maleate; where Q= (H$_3$C)$_2$CHN,

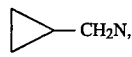

C$_6$H$_5$CH$_2$N or n-C$_3$H$_7$N and or Y=(H$_3$C)$_2$CHN, C$_6$H$_5$CH$_2$N with the proviso that when either one of Q or Y is C$_6$H$_5$CH$_2$N, then the other Q or Y group cannot be (H$_3$C)$_2$CHN or C$_6$H$_5$CH$_2$N.

2. 3-Alkyl-7-substituted-9,9-(1,3-dithiolan-2-yl)-3-azabicyclo[3.3.1]nonanes characterized by the formula:

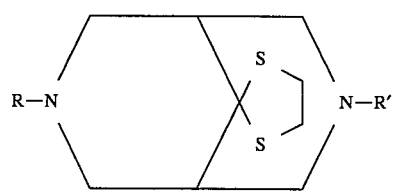

[With and without HX and 2 HX]

wherein

X= ClO$_4$, Br, Cl, HSO$_4$, citrate, fumarate, or maleate; R=(H$_3$C)$_2$CH— or cyclopropylmethyl and R'= (H$_3$C)$_2$CH— or C$_6$H$_5$CH$_2$—.

3. 3-Alkyl-7-substituted-3-azabicyclo[3.3.1] nonanes characterized by the formula:

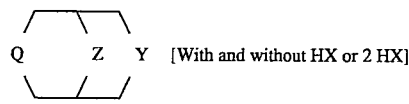  [With and without HX or 2 HX]

wherein

X=ClO$_4$, Cl, Br, HSO$_4$, titrate, fumarate, or maleate; Q=(H$_3$C)$_2$CHN;
Z= CH$_2$; and
Y=4-O$_2$N—C$_6$H$_4$—C(O)N, 4-H$_2$N—C$_6$H$_4$—C(O)N, 4-AcHNC$_6$H$_4$—C(O)N, 4—H$_3$CSO$_2$NH—C$_6$H$_4$—C(O)N, 4-F—C$_6$H$_4$—C(O)N, 4-O$_2$N—C$_6$H$_4$CH$_2$C(O)N, 4-H$_2$N—C$_6$H$_4$CH$_2$C(O)N, 4—AcHNC$_6$H$_4$CH$_2$C(O)N, 4-H$_3$CSO$_2$NHC$_6$H$_4$CH$_2$C(O)N,

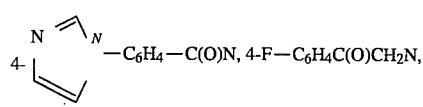

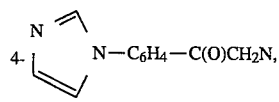

-continued

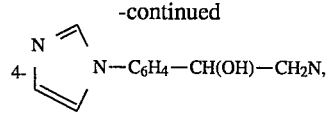

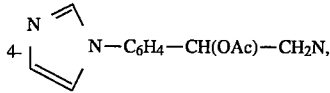

or (H$_3$C)$_2$CHN.

4. 3-Alkyl-7-substituted-3-azabicyclo[3.3.1] nonanes characterized by the formula:

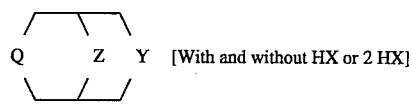  [With and without HX or 2 HX]

wherein

X=ClO$_4$, Cl, Br, HSO$_4$, citrate, fumarate, or maleate; Q=

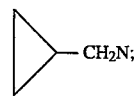

Z=CH$_2$; and   Y=4-H$_2$N—C$_6$H$_4$CH$_2$C(O)N, 4-AcHNC$_6$H$_4$CH$_2$C(O)N, 4-H$_3$CSO$_2$NH—C$_6$H$_4$-C(O)N,

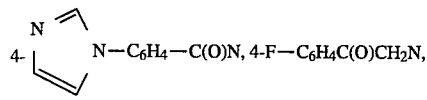

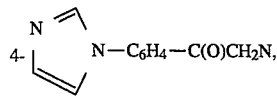

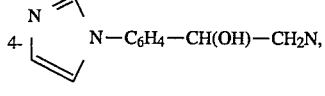

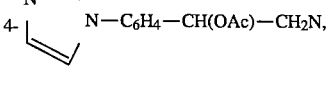

(H$_3$C)$_2$CHN, or C$_6$H$_5$CH$_2$N.

5. 3-Alkyl-7-substituted-3-azabicyclo[3.3.1] nonanes characterized by the formula:

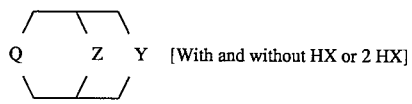  [With and without HX or 2 HX]

wherein

X=ClO$_4$, Cl, Br, HSO$_4$, citrate, fumarate, or maleate; Q=n-C$_3$H$_7$N;
Z= CH$_2$; and
Y=4-O$_2$N—C$_6$H$_4$—C(O)N, 4-H$_2$N—C$_6$H$_4$—C(O)N, 4-AcHNC$_6$H$_4$—C(O)N, 4-H$_3$CSO$_2$NH—C$_6$H$_4$—

C(O)N, 4-F—C$_6$H$_4$-C(O)N, 4-O$_2$N—C$_6$H$_4$CH$_2$C(O)N,
4-H$_2$N—C$_6$H$_4$CH$_2$C(O)N, 4-AcHNC$_6$H$_4$CH$_2$C(O)N,
4-H$_3$CSO$_2$NHC$_6$H$_4$CH$_2$C(O)N,
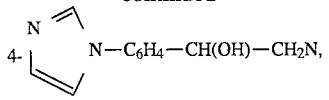
4- N—C$_6$H$_4$—C(O)N, 4-F—C$_6$H$_4$C(O)CH$_2$N,
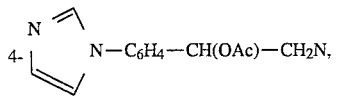
4- N—C$_6$H$_4$—C(O)CH$_2$N,
-continued
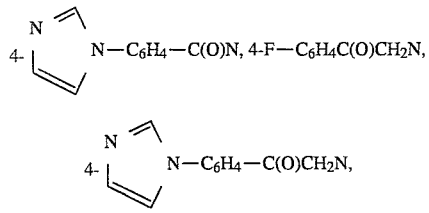
4- N—C$_6$H$_4$—CH(OH)—CH$_2$N,
4- N—C$_6$H$_4$—CH(OAc)—CH$_2$N,
(H$_3$C)$_2$CHN, or C$_6$H$_5$CH$_2$N.
* * * * *